US009433664B2

(12) United States Patent
Lovgren et al.

(10) Patent No.: US 9,433,664 B2
(45) Date of Patent: Sep. 6, 2016

(54) FACTOR II AND FIBRINOGEN FOR TREATMENT OF HAEMOSTATIC DISORDERS

(75) Inventors: Ann Lovgren, Molndal (SE); Kenny Hansson, Molndal (SE)

(73) Assignee: MEDIMMUNE LIMITED, Cambridge (GB)

( * ) Notice: Subject to any disclaimer, the term of this patent is extended or adjusted under 35 U.S.C. 154(b) by 108 days.

(21) Appl. No.: 13/877,854

(22) PCT Filed: Sep. 19, 2011

(86) PCT No.: PCT/EP2011/066241
§ 371 (c)(1),
(2), (4) Date: Jun. 24, 2013

(87) PCT Pub. No.: WO2012/045569
PCT Pub. Date: Apr. 12, 2012

(65) Prior Publication Data
US 2013/0280236 A1    Oct. 24, 2013

Related U.S. Application Data

(60) Provisional application No. 61/390,224, filed on Oct. 6, 2010.

(51) Int. Cl.
*A61K 38/48* (2006.01)
*A61K 38/36* (2006.01)
(52) U.S. Cl.
CPC ......... *A61K 38/4833* (2013.01); *A61K 38/363* (2013.01); *A61K 38/4846* (2013.01)
(58) Field of Classification Search
None
See application file for complete search history.

(56) References Cited

U.S. PATENT DOCUMENTS

| | | | |
|---|---|---|---|
| 4,501,731 A | 2/1985 | Tishkoff et al. | |
| 5,866,122 A | 2/1999 | Turecek et al. | |
| 6,039,945 A | 3/2000 | Turecek et al. | |
| 2003/0129183 A1 | 7/2003 | Spillert | |
| 2004/0198647 A1 | 10/2004 | Hess | |
| 2004/0237970 A1 | 12/2004 | Vournakis | |
| 2005/0282771 A1 | 12/2005 | Johnson | |
| 2006/0025336 A1 | 2/2006 | Rojkjaer | |
| 2006/0159733 A1* | 7/2006 | Pendharkar et al. ......... 424/445 |
| 2006/0211621 A1 | 9/2006 | Knudsen | |
| 2007/0232788 A1 | 10/2007 | Saenko | |
| 2008/0014251 A1 | 1/2008 | Benz | |
| 2008/0188400 A1 | 8/2008 | Ropke | |
| 2008/0267940 A1 | 10/2008 | Mohammed | |
| 2009/0098103 A1 | 4/2009 | Madison | |
| 2009/0148502 A1 | 6/2009 | Pronovost | |
| 2009/0175931 A1 | 7/2009 | Camire | |
| 2009/0232877 A1 | 9/2009 | Montes | |
| 2010/0086529 A1 | 4/2010 | Mohammad | |
| 2010/0093607 A1 | 4/2010 | Dickneite | |

FOREIGN PATENT DOCUMENTS

| | | |
|---|---|---|
| AU | 2003204479 A1 | 6/2003 |
| CN | 1867669 A | 11/2006 |
| EP | 1935429 A1 | 6/2008 |
| JP | H07145075 A | 6/1995 |
| JP | H08059505 A | 8/1995 |
| JP | H10045620 A | 2/1998 |
| JP | 2001517636 A | 10/2001 |
| JP | 2007508820 A | 4/2007 |
| JP | 2010513349 A | 4/2010 |
| RU | 2298416 | 5/2007 |
| WO | 8102105 | 8/1981 |
| WO | 9915196 | 4/1999 |
| WO | 2003007983 | 1/2003 |
| WO | WO-2005038019 A1 | 4/2005 |
| WO | WO 2007103447 A2 * | 9/2007 |
| WO | 2008077529 A1 | 7/2008 |
| WO | WO-2012045569 A1 | 4/2012 |

OTHER PUBLICATIONS

Fries et al. (British J Anaesthesia, 97 (4); 460-7, 2006.*
Abdel-Wahab, Omar I., "Effect of fresh-frozen plasma transfusion on prothrombin time and bleeding in patients with mild coagulation abnormalities", Transfusion;46(8), (Aug. 2006), 1279-1285.
Al Dieri Raed, "The thrombogram in rare inherited coagulation disorders: its relation to clinical bleeding", Journal of Thrombosis and Haemostasis;88, (2002), 576-582.
Bagot, Catherine N., "Perioperative myocardial infarction in a patient receiving low-dose prothrombin complex concentrates", Thrombosis and Haemostasis;98, (2007), 1141-1142.
Blome Markus, "Relationship between factor XIII activity, fibrinogen, haemostasis screening tests and postoperative bleeding in cardiopulmonary bypass surgery", Journal of Thrombosis and Haemostasis,93, (2005), 1101-1107.
Brohi Karim, "Acute traumatic coagulopathy", Journal of Trauma,54, (2003), 1127-1130.
Charbit B., "The decrease of fibrinogen is an early predictor of the severity of postpartum hemorrhage", Journal of Thrombosis and Haemostasis,5, (2007), 266-273.
Chowdhury Pratima, "Efficacy of standard dose and 30 ml/kg fresh frozen plasma in correcting laboratory parameters of haemostasis in critically ill patients", British Journal of Haematology, 125, (2004), 69-73.
Ciavarella D., "Clotting factor levels and the risk of diffuse microvascular bleeding in the massively transfused patient", British Journal of Haematology, 67, (1987), 365-368.
Dara, Saqib I., "FFP transfusion in critically ill medical patients with coagulopathy", Critical Care Medicine, 33, (2005), 2667-2671.

(Continued)

*Primary Examiner* — Amber D Steele
*Assistant Examiner* — Schuyler Milton
(74) *Attorney, Agent, or Firm* — Melissa J. Pytel

(57) ABSTRACT

The present invention relates to normalizing impaired haemostasis comprising administering a clotting factor treatment selected from the group consisting of (1) FII; (2) PCC; and (3) a three factor combination of FH, FX and FVIIa. The clotting factor treatment can be administered in combination with fibrinogen. The clotting factor(s) can be recombinant human clotting factor(s).

16 Claims, 12 Drawing Sheets

(56) References Cited

OTHER PUBLICATIONS

Dickneite G., "Characterization of the coagulation deficit in porcine dilutional coagulopathy and substitution with a prothrombin complex concentrate", Anesthesia & Analgesia, 106, (Apr. 2008), 1070-1077.

Dickneite G., "Prothrombin complex concentrate vs fresh frozen plasma for reversal of dilutional coagulopathy in a porcine trauma model", British Journal of Anaesthesia, 102, (2009), 345-354.

Fenger-Eriksen C., "Fibrinogen substitution improves whole blood clot firmness after dilution with hydroxyethyl starch in bleeding patients undergoing radical cystectomy: a randomized, placebocontrolled clinical trial", Journal of Thrombosis and Haemostasis, 7, (2009), 795-802.

Fenger-Eriksen C., "Mechanisms of hydroxyethyl starch-induced dilutional coagulopathy", Journal of Thrombosis and Haemostasis, 7, (2009), 1099-1105.

Franchini Massimo, "Prothrombin complex concentrates: an update", Blood Transfusion, 8(3), (2010), 149-154.

Fries D., "Effect of fibrinogen on reversal of dilutional coagulopathy: a porcine model", British Journal of Anaesthesia, 95, (2005), 172-177.

Fries D., "Efficacy of fibrinogen and prothrombin complex concentrate used to reverse dilutional coagulopathy—a porcine model", British Journal of Anaesthesia, 97(4), (2006), 460-467.

Fries Dietmar, "The effect of fibrinogen substitution on reversal of dilutional coagulopathy: an in vitro study", Anesthesia & Analgesia, 102, (2006), 347-351.

Fries Dietmar, "The effect of the combined administration of colloids and lactated Ringer's solution on the coagulation system: an in vitro study using thrombelastograph coagulation analysis (ROTEG)", Anesthesia & Analgesia, 94, (2002), 1280-1287.

Gerlach Rudiger, "Increased risk for postoperative hemorrhage after intracranial surgery in patients with decreased Factor XIII activity: implications of a prospective study", Stroke, 33, (2002), 1618-1623.

Hiippala, Seppo T., "Hemostatic factors and replacement of major blood loss with plasma-poor red cell concentrates", Anesthesia & Analgesia, 81, (1995), 360-365.

Innerhofer Petra, "The effects of perioperatively administered colloids and crystalloids on primary platelet-mediated hemostasis and clot formation", Anesthesia & Analgesia, 95, (2002), 858-865.

Iorio A., "Recombinant Factor Vila concentrate versus plasma derived concentrates for the treatment of acute bleeding episodes in people with haemophilia and inhibitors", Cochrane Database of Systematic Reviews, (8), (2004), 1-20.

Kohler Michael, "Thromboembolic complications associated with the use of prothrombin complex and factor IX concentrates", Thrombosis and Haemostasis, 80, (1998), 399-402.

Korte W., "Fibrin monomer and factor XIII: a new concept for unexplained intraoperative coagulopathy", Hämostaseologie, 26, (2006), S30-S35.

Lier H., "Coagulation management in multiple trauma: a systematic review", Intensive Care Med, 37, (2011), 572-582.

Lier H., "Coagulation management in the treatment of multiple trauma", Journal of Anesthesia, Intensive Care, Emergency and Civil Medicine Pain Medicine, Springer, Berlin, DE, 2009;58(10), (2009), 1010-1026.

Luddington R.J., "Thrombelastography/thromboelastometry", Clinical & Laboratory Haematology, 27, (2005), 81-90.

McLoughlin Jr., Thomas M., "Profound normovolemic hemodilution: hemostatic effects in patients and in a porcine model", Anesthesia & Analgesia, 83, (1996), 459-465.

Mittermayr Markus, "Haemostatic changes after crystalloid or colloid fluid administration during major orthopaedic surgery: the role of fibrinogen administration", Anesthesia & Analgesia, 105, (Oct. 2007), 905-917.

Sarani Babak, "Transfusion of fresh frozen plasma in critically ill surgical patients is associated with an increased risk of infection", Critical Care Medicine, 36, (2008), 1114-1118.

Scalea, Thomas M., "Early aggressive use of fresh frozen plasma does not improve outcome in critically injured trauma patients", Annals of Surgery, 248, (Oct. 2008), 578-584.

Schöchl H., "Use of rotation thromboelastometry (ROTEM) to achieve successful treatment of polytrauma with fibrinogen concentrate and prothrombin complex concentrate", Anaesthesia, 65(2), (2010), 199-203.

Singbartl Kai, "Hemostasis and Hemodilution: A Quantitative Mathematical Guide for Clinical Practice", Anesthesia & Analgesia, 96, (2003), 929-935.

Spahn, Donat R., "Management of bleeding following major trauma: a European Guideline", Critical Care, 11:R17, (2007), 1-22.

Sperry, Jason L., "Early use of vasopressors after injury: Caution before constriction", Journal of Trauma, 64, (Jan. 2008), 9-14.

Stainsby D., "Guidelines on the management of massive blood loss", British Committee for Standards in Haematology, British Journal of Haematology, 135, (2006), 634-641.

Stainsby D., "Management of massive blood loss: a template guideline", British Journal of Anaesthesia, 85, (2000), 487-491.

Stanworth S. J., "Is fresh frozen plasma clinically effective? A systematic review of randomised controlled trials", British Journal of Haematology, 126, (2004), 139-152.

Staudinger T., "Influence of prothrombin complex concentrates on plasma coagulation in critically ill patients", Intensive Care Medicine, 25, (1999), 1105-1110.

Stinger, Harry K., "The ratio of fibrinogen to red cells transfused affects survival in casualties receiving massive transfusions at an army combat support hospital", Journal of Trauma, 64, (2008), S79-S85.

Ucar, Halil Ibrahim, "Preoperative fibrinogen levels as a predictor of postoperative bleeding after open heart surgery", Heart Surgery Forum, 10, (2007), E392-E396.

Velik-Salchner Corinna, "Normal values for thrombelastography (ROTEM) and selected coagulation parameters in porcine blood", Thrombosis Research, 117, (2006), 597-602.

Velik-Salchner Corinna, "The effect of fibrinogen concentrate on thrombocytopenia", Journal of Thrombosis and Haemostasis, 5, (2007), 1019-1025.

Warren Otis, "Massive, fatal, intracardiac thrombosis associated with prothrombin complex concentrate", Annals of Emergency Medicine, 53, (Jun. 2009), 758-761.

Watson Gregory A., "Fresh frozen plasma is independently associated with a higher risk of multiple organ failure and acute respiratory distress syndrome", Journal of Trauma, 67, (Aug. 2009), 221-227.

Naito et al., "Activation of human blood coagulation factor XI independent of factor XII. Factor XI is activated by thrombin and factor XIa in the presence of negatively charged surfaces." The Journal of Biological Chemistry, vol. 266, 1991, pp. 7353-7358.

Sun et al., "Vitamin K epoxide reductase significantly improves carboxylation in a cell line overexpressing factor X", Blood, 106(12):3811-3813 (2005).

* cited by examiner

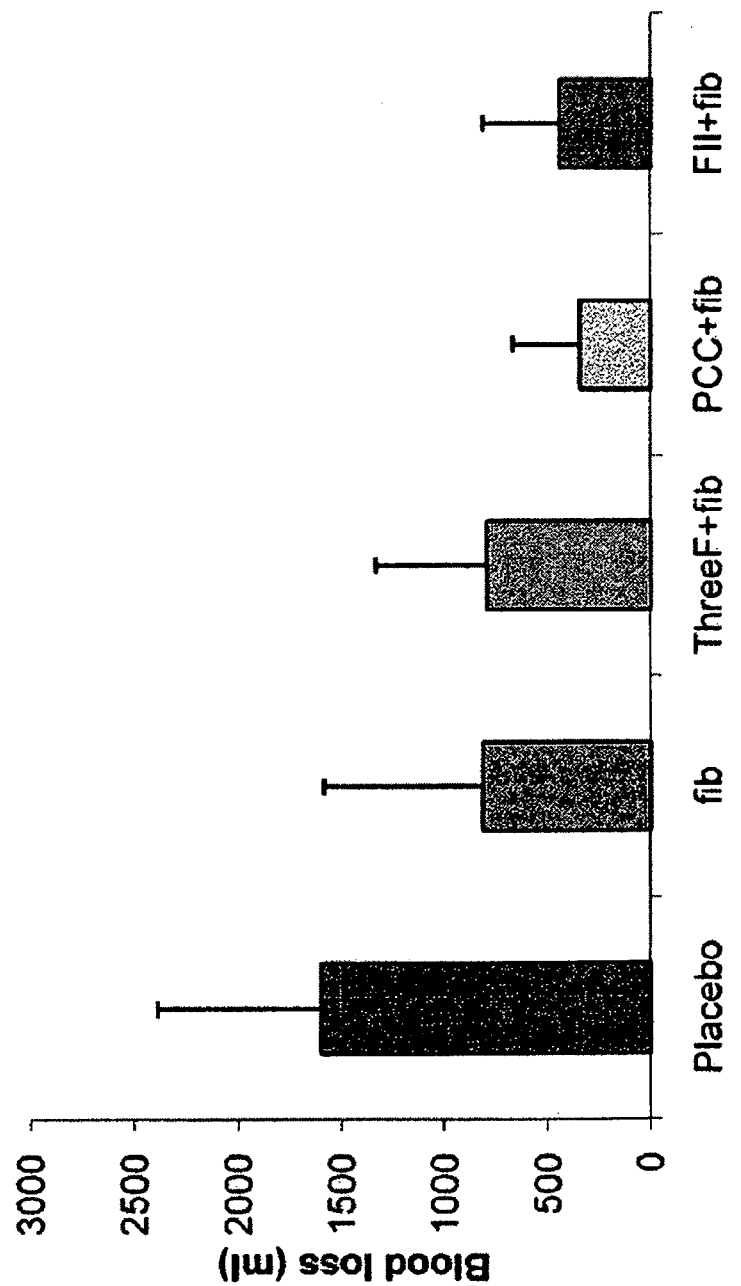

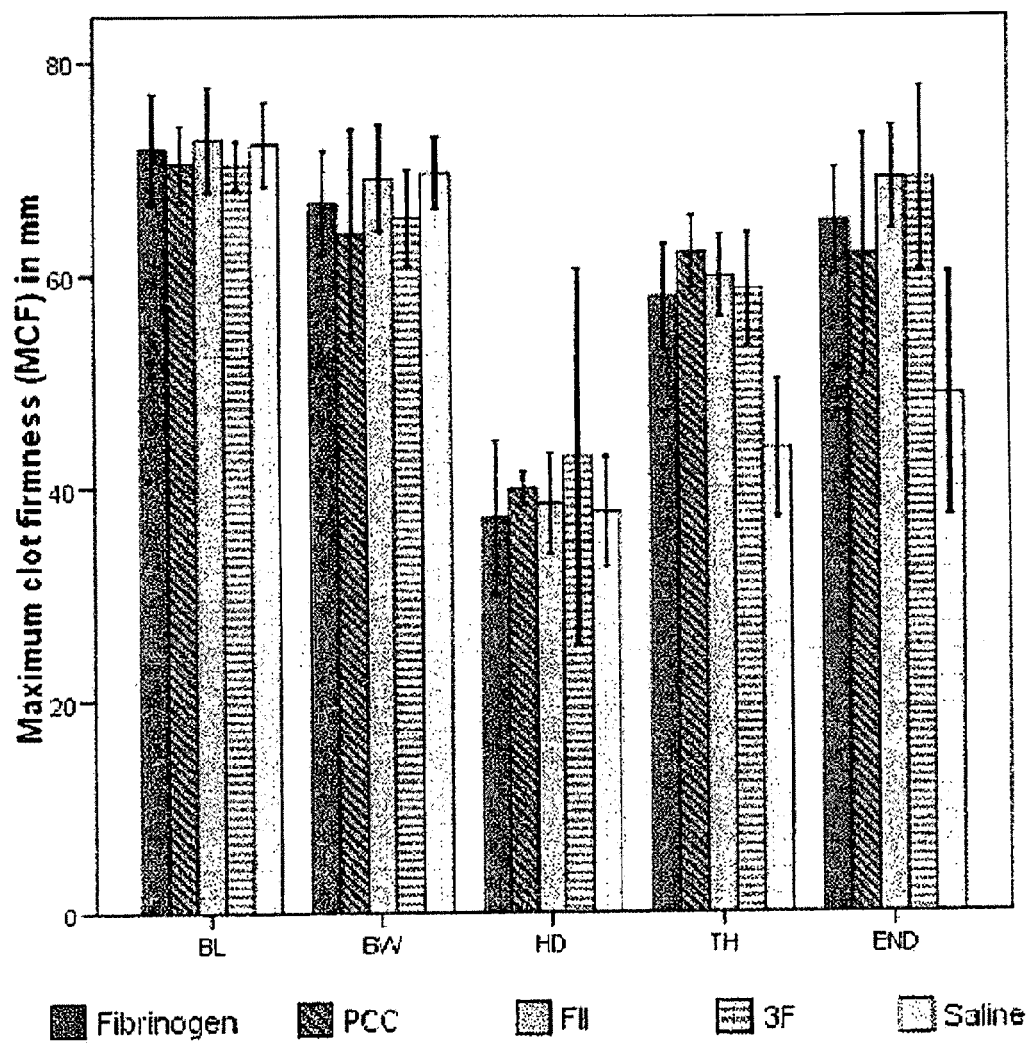

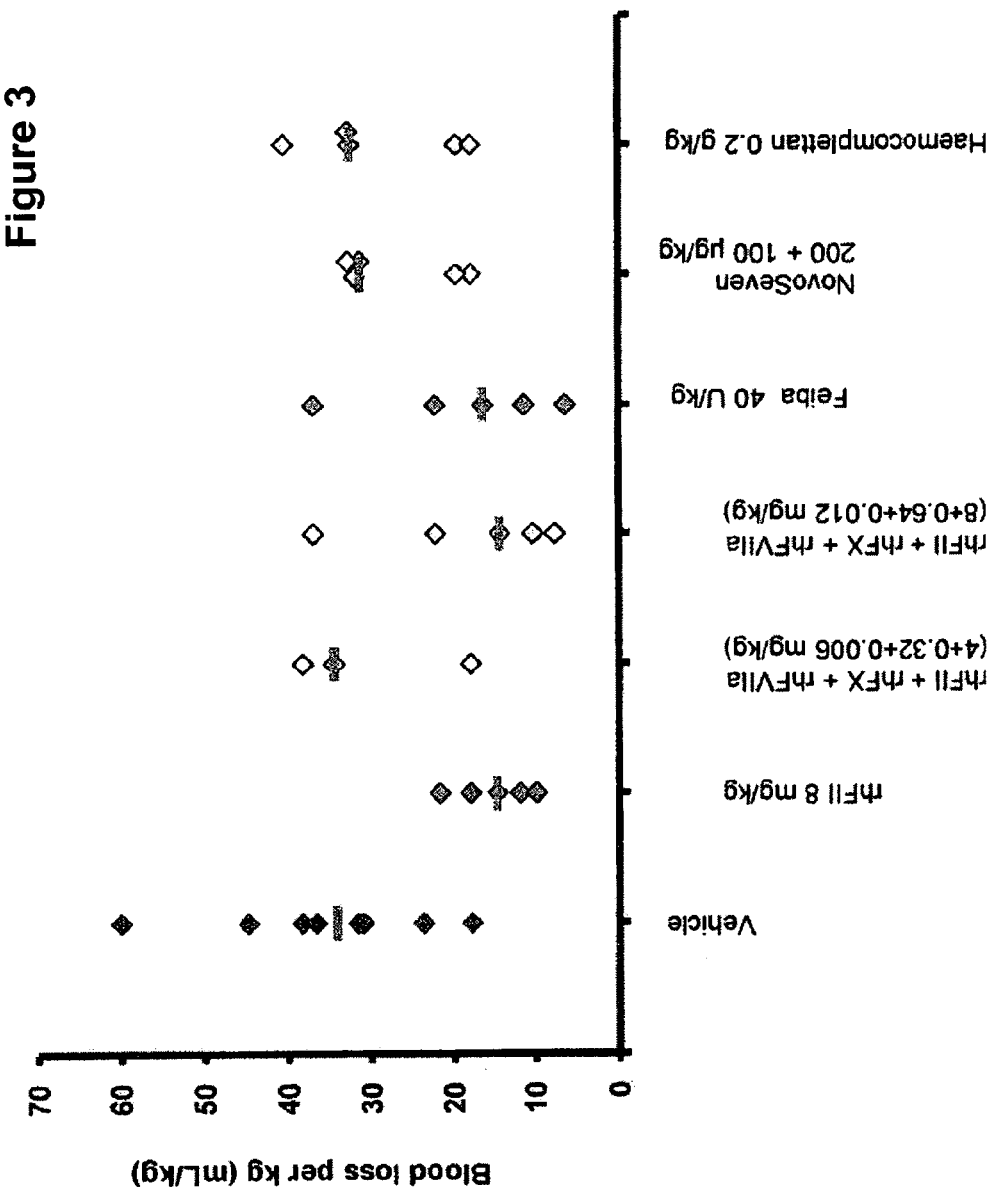

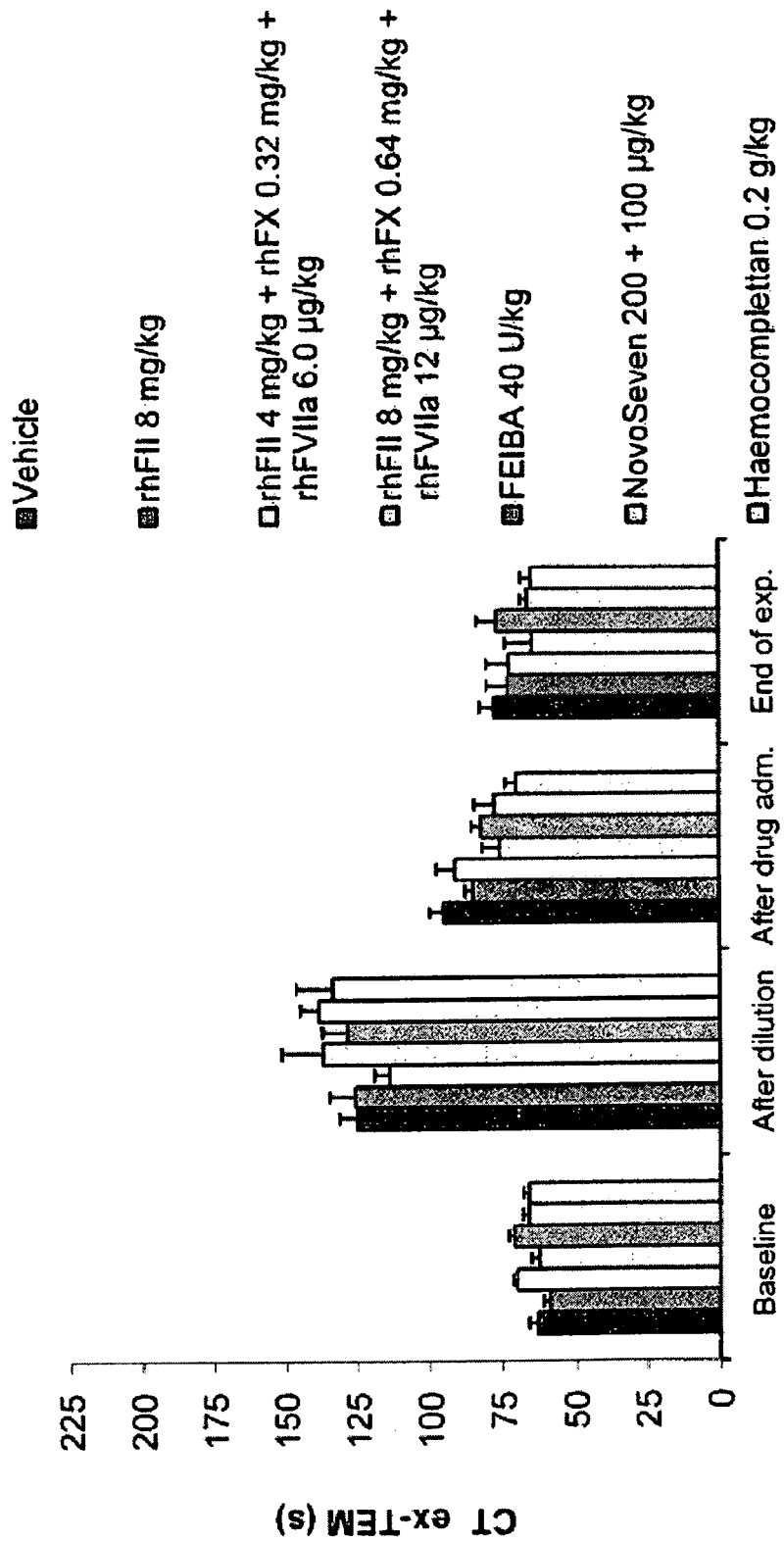

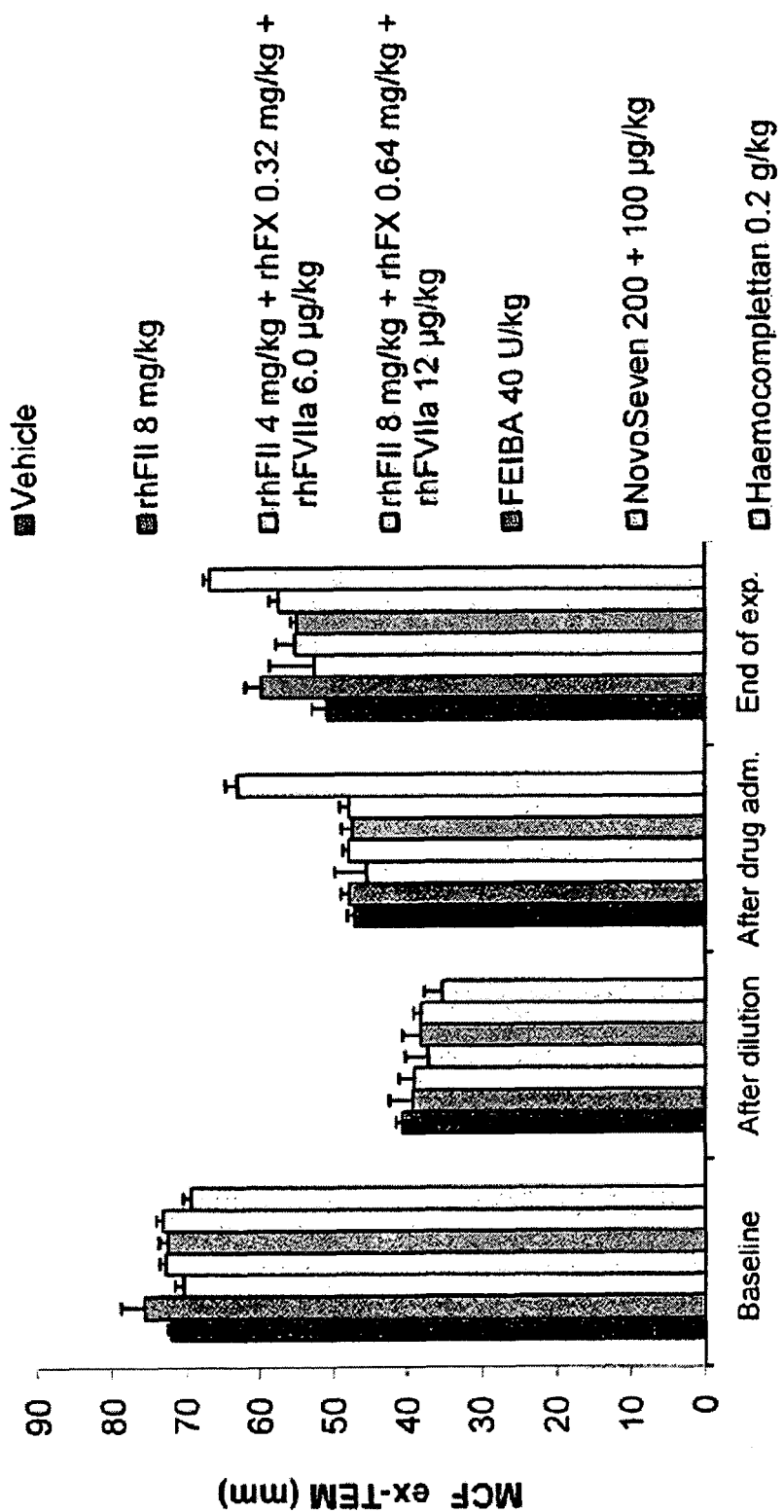

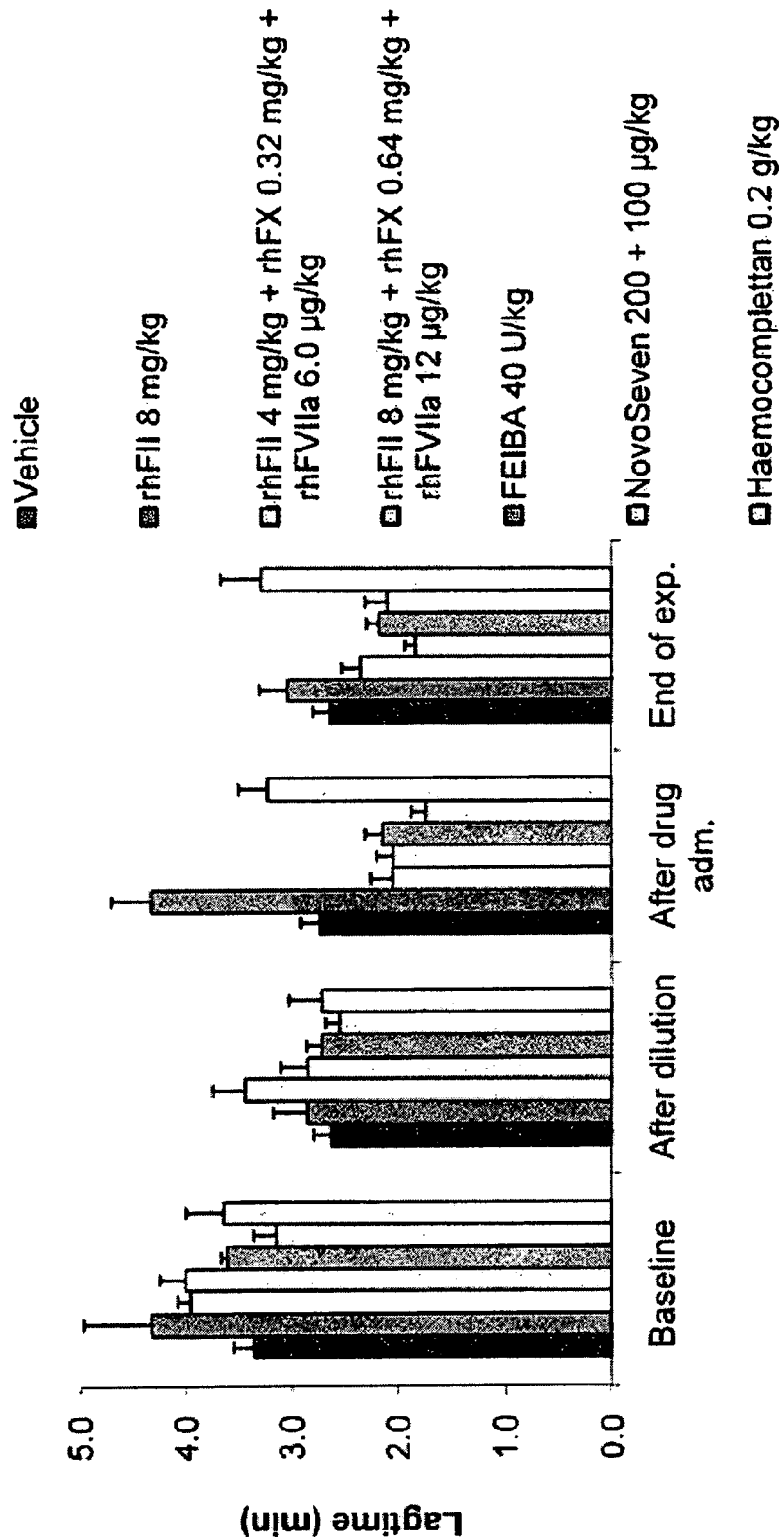

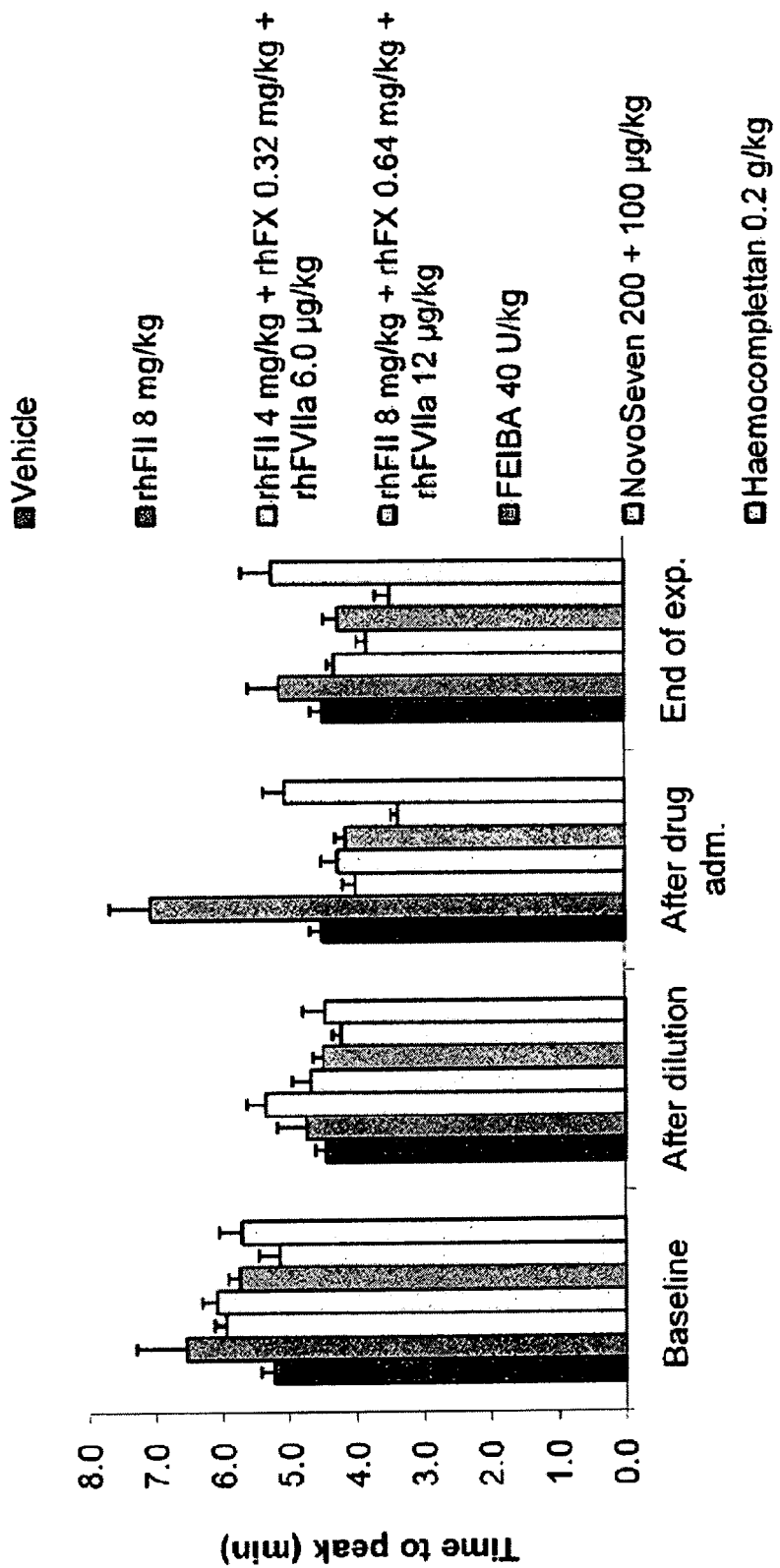

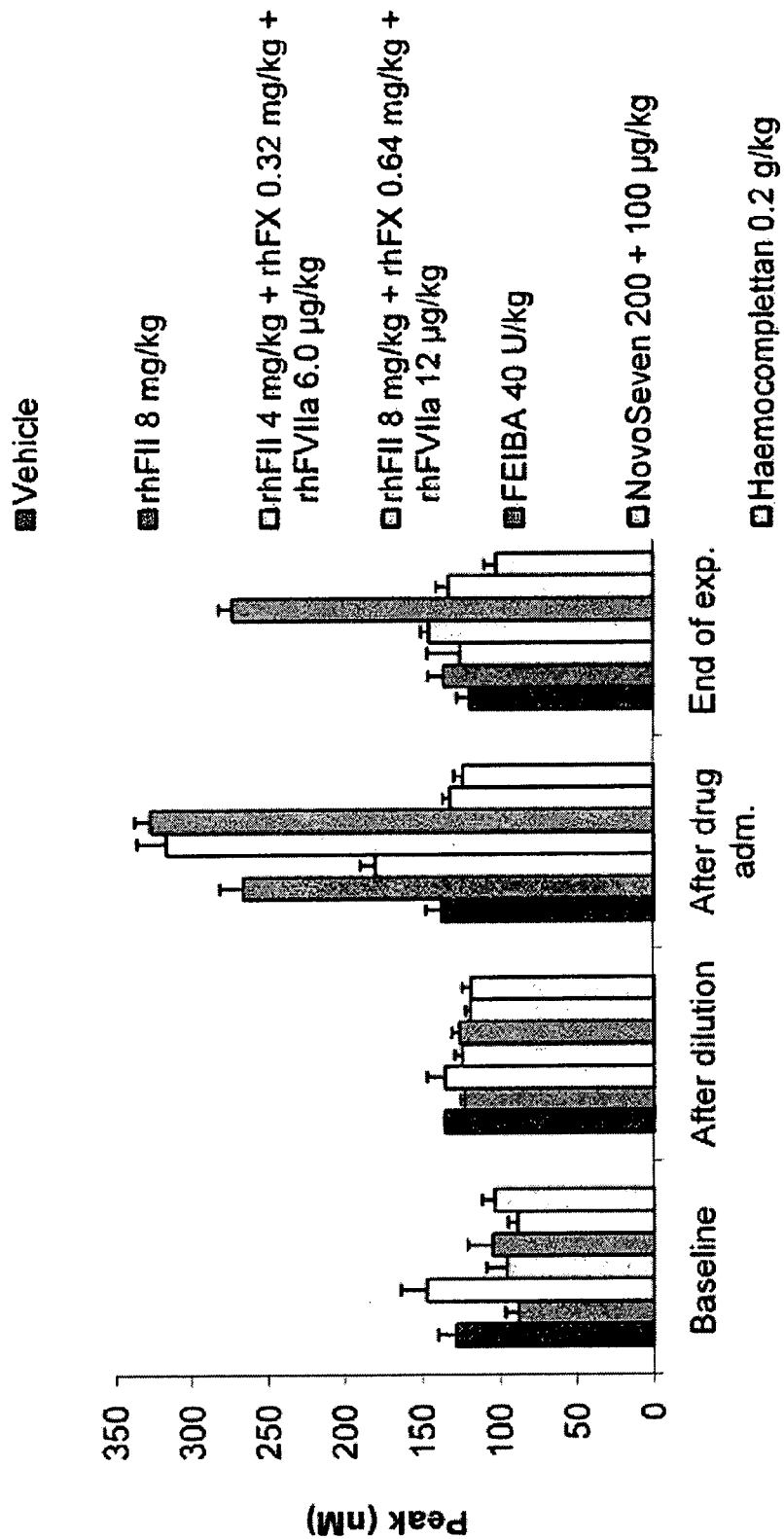

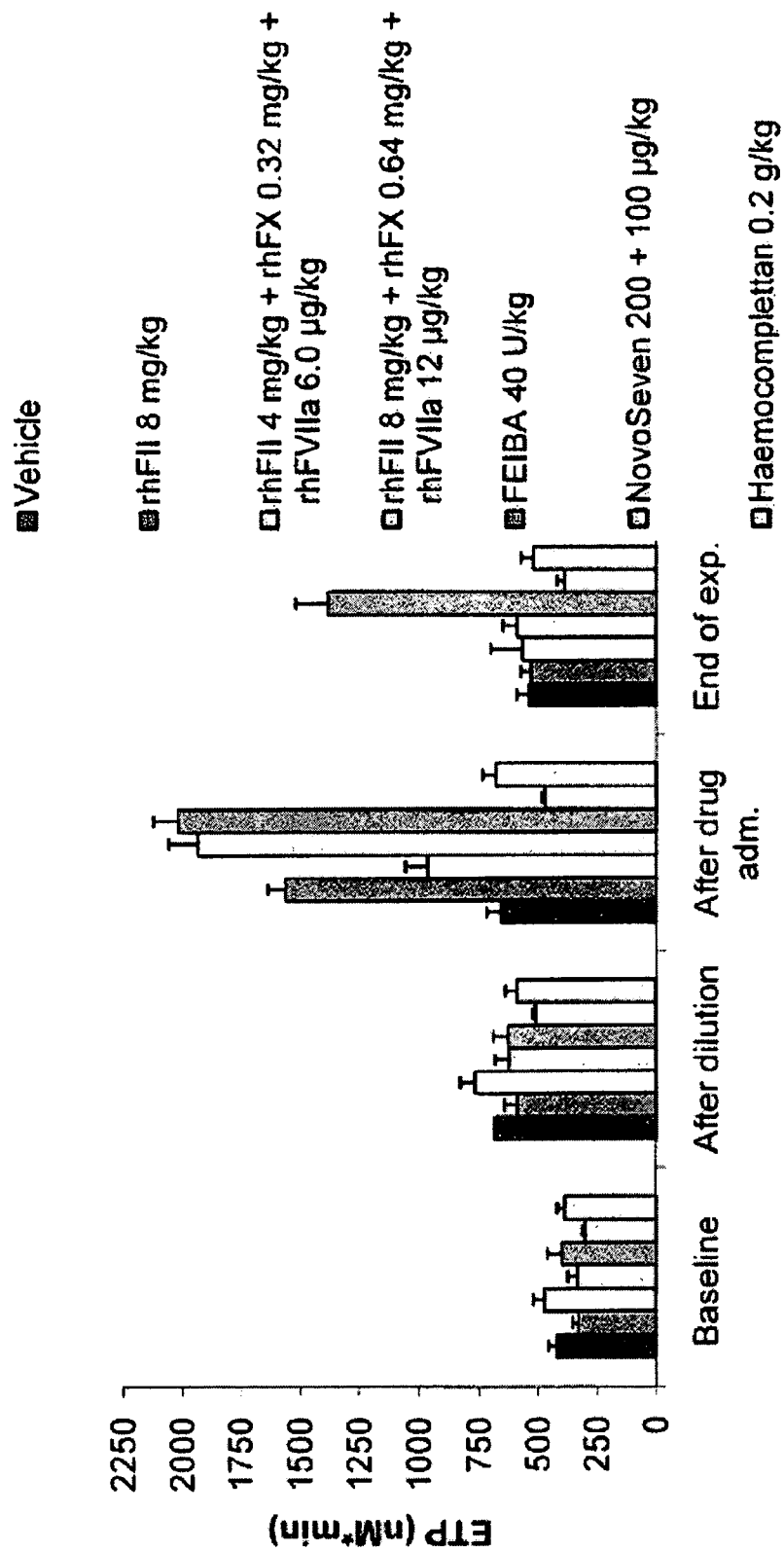

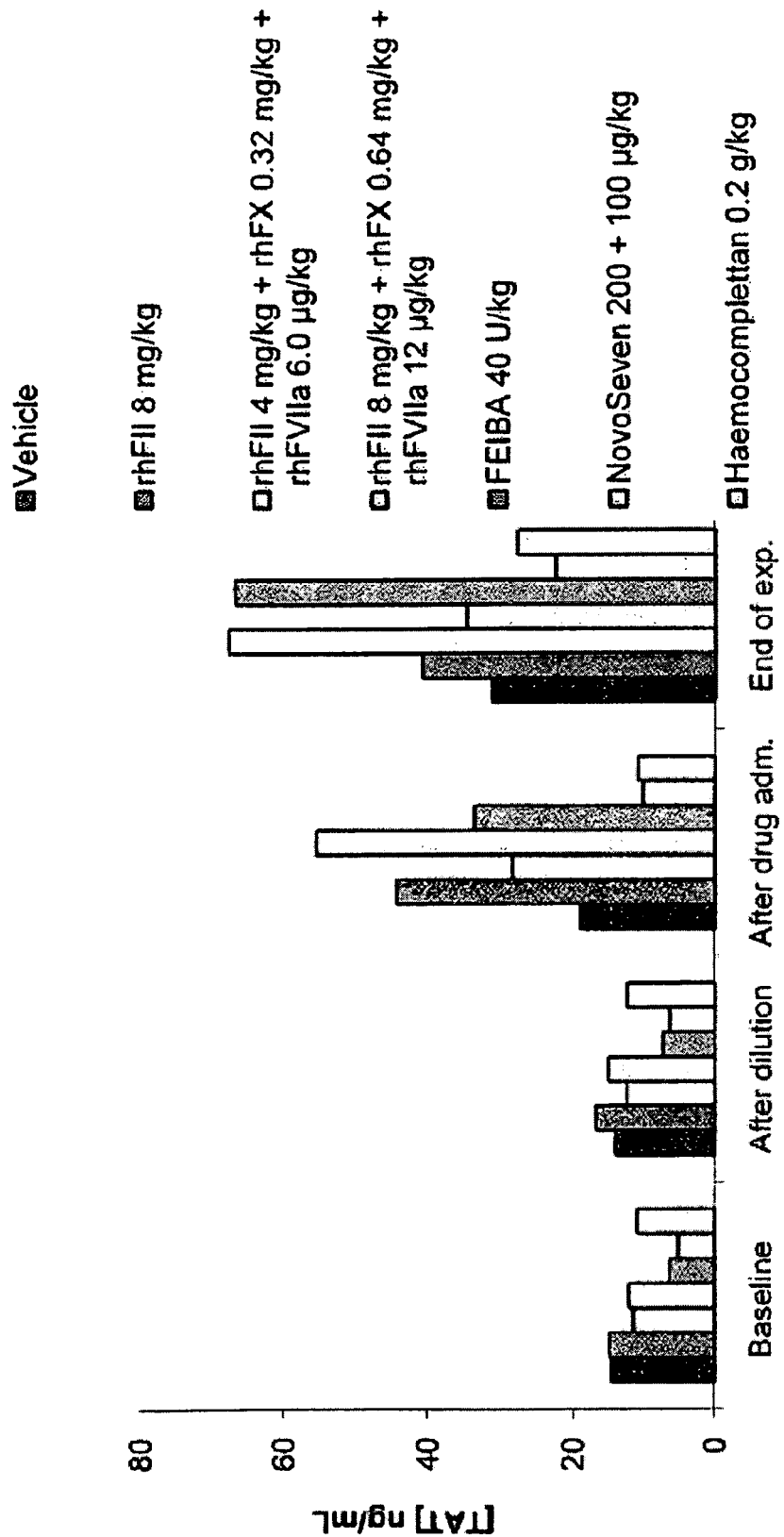

FACTOR II AND FIBRINOGEN FOR TREATMENT OF HAEMOSTATIC DISORDERS

CROSS-REFERENCE TO RELATED APPLICATIONS

This application is a U.S. National Stage application of International Application No. PCT/EP2011/066241, filed on Sep. 19, 2011, said International Application No. PCT/EP2011/066241 claims benefit under 35 U.S.C. §119(e) of the U.S. Provisional Application No. 61/390,224, filed Oct. 6, 2010. Each of the above listed applications is incorporated by reference herein in its entirety for all purpose.

BACKGROUND

1. Field

This disclosure relates to methods of treating haemostatic disorders.

2. Description of the Related Art

Haemostasis refers to the process of stopping blood loss from a damaged blood vessel. Coagulation, or the formation of blood clots, is an important part of haemostasis. To stop bleeding from a wound, a damaged blood vessel wall is covered by a clot containing platelets and fibrin. Disorders of coagulation can lead to an increased risk of bleeding (hemorrhage) or clotting (thrombosis).

Massive bleeding or transfusion in patients is commonly associated with impaired coagulation. This impaired coagulation can be caused by dilutional coagulopathy, defined as increased bleeding tendency due to dilution of the blood. Fluid compensation is a conventional treatment of extensive blood loss to normalize blood pressure and avoid circulatory shock. However, fluid compensation dilutes the coagulation factors in the remaining blood and impairs their function, which can result in increased bleeding that might be life-threatening.

The in vivo biochemical pathways leading to coagulation are complex and require a large number of factors and cofactors. There are ten factors designated by Roman numerals I-XIII with III, IV and VI being unused designators. Numerous related factors and cofactors modulate the activity of the biochemical pathway. For example, in the tissue factor pathway, following damage to he blood vessel, factor VII (abbreviated FVII as is the convention for the Roman numeral denominated factors) comes into contact with tissue factor (TF) expressed on tissue-factor-bearing cells (stromal fibroblasts and leukocytes). This forms an activated complex (TF-FVIIa), TF-FVIIa activates FIX and FX. FVII is itself activated by thrombin, FXIa, plasmin, FXII, and FXa. The conversion of FX to activated FXa by TF-FVIIa is almost immediately inhibited by tissue factor pathway inhibitor (TFPI). FXa and its co-factor FVa form the prothrombinase complex, which activates pro-throbin to thrombin. Thrombin then activates other components of the coagulation cascade, including FV and FVIII (which activates FXI, which, in turn, activates FIX), and activates and releases FVIII from being bound to von Willebrand factor (vWf). FVIIIa is the co-factor of FIXa, and together they form the "tenase" complex, which activates FX to positively feed back into the cycle. Activation of the pathway produces a burst of activated thrombin. The thrombin activated in this cycle can convert fibrinogen to fibrin which is the protein which forms a clot together with platelets.

Prothrombin (FII) is produced in the liver and is post-translationally modified in a vitamin K-dependent reaction that converts ten glutamic acids on prothrombin to gamma carboxy glutamic acid. Deficiency of vitamin K or administration. of the anticoagulant warfarin inhibits the conversion of Factor II glutamic acid residue to Gla, slowing the activation of the coagulation cascade. Thrombin (FIIa) is produced by enzymatic cleavage of two sites on FII by activated Factor X (FXa). The activity of FXa is greatly enhanced by binding to activated Factor V (FVa). In human adults the normal blood level of prothrombin activity has been measured to be around 1.1 units/ml. Newborn plasma levels of prothrombin steadily increase after birth to reach normal adult levels, from a level of around 0.5 units/ml one day after birth, to a level of around 0.9 units/ml after 6 months of life, Thrombin, which is formed from prothrombin, has many effects in the coagulation cascade. It is a serine protease that converts soluble fibrinogen into insoluble strands of fibrin, as well as catalyzing many other coagulation-related reactions. Al Dieri et al. investigated the relationship between clotting factor concentrations, parameters of thrombin generation, and the amount of blood loss in patients with various congenital coagulation factor deficiencies. The authors demonstrated that bleeding tendency was directly associated with the amount of thrombin generation, which varied linearly with the FII concentrations. Al Dieri et al. *Thromb Haemost* 2002, 88:576-82. Fenger-Erikson et al. also showed, in the case of dilutional coagulopathy, that aside from fibrinogen, coagulation factors including FII, FX , and FXIII also decrease below the expected level following a 32% dilution with hydroxyethyl starch solution. Fenger-Eriksen et al, *J Thromb Haemost* 2009, 7:1099-105.

Fibrinogen (Factor I or FI) is a soluble plasma glycoprotein that is synthesized by the liver and converted by thrombin into fibrin during blood coagulation. Processes in the coagulation cascade convert pro-thrombin to the activated serine protease thrombin, which converts fibrinogen into fibrin. Fibrin is then cross-linked by factor XIII to form a clot. The normal concentration of fibrinogen in blood plasma is 1.5-4.0 g/L or about 7 µM. In the event of marked blood loss, fibrinogen more than any other procoagulant factors or platelets reaches critically low plasma concentrations. Hiippala et al. *Anesth Analg* 1995, 81:360-5; Singbartl et al. *Anesth Analg* 2003, 96:929-35; McLoughlin et al. *Anesth Analg* 1996, 83:459-65. Small quantities of colloids (less than 1000 ml) can impair fibrin polymerization and thus clot strength. Innerhofer P et al., *Anesth Analg* 2002, 95:858-65; Mittermayr et al. *Anesth Analg* 2007; 105:905-17; Fries et al. *Anesth Analg* 2002, 94:1280-7. Some recommendations quote a threshold fibrinogen concentration of 1 g/L based on the results of a study in which four out of four patients with a fibrinogen concentration of less than 0.5 g/L were seen to have diffuse microvascular bleeding. Spahn et al., *Crit Care* 2007, 11:R17; Stainsby et al. *Br J Haematol* 2006; 135:634-41; Ciavarella et al. *Br J Haematol* 1987; 67:365-8. By contrast, recent clinical data from peripartal hemorrhage, neurosurgery and cardiac surgery show that at a fibrinogen concentration of less than 1.5-2 g/L, there is already an increased tendency for peri- and postoperative bleeding. Charbit et al, *J Thromb Haemost* 2007, 5:266-73; Gerlach et al. *Stroke* 2002, 33:1618-23; Blome et al. *J Thromb Haemost* 2005, 93:1101-7; Ucar et al. *Heart Surg Forum* 2007, 10:E392-6.

Coagulation problems associated with bleeding disorders such as dilutional coagulopathy can be addressed with haemostatic therapy. The aim of haemostatic therapy is to minimize blood loss, transfusion requirements, and mortality. In trauma patients with identical Injury Severity Scores (ISS), mortality virtually doubles simply as a result of coagulopathy. Brohi et al. *J Trauma* 2003, 54:1127-30. Massive bleeding or massive transfusion in multi-traumatized patients is associated with impaired coagulation. Thus, to achieve adequate haemostasis, a sufficient amount of thrombin and sufficient coagulable substrate are required. Key elements in coagulation are the formation of thrombin on the platelet surface and the cleavage of fibrinogen by thrombin to form fibrin. Brohi et al *Trauma* 2003, 54:1127-30. If sufficient thrombin is formed, it converts fibrinogen to stable fibrin, which determines the firmness of the developing clot in the presence of factor XIII (FXIII). Korte, et al., *Hamostaseologie* 2006, 26:S30-5.

Aggressive fluid replacement is crucial in th.e case of massive blood loss, in patients with blunt and multiple trauma, to maintain normovolemia. Sperry J L, et al. *J Trauma* 2008; 64:9-14. However, haemodynamic stabilization by administering large amounts of crystalloid or colloid solutions causes dilutional coagulopathy. The clinical effects of impaired plasma clotting caused by normovolemic haemodilution were previously investigated in several publications. Innerhofer P et al. *Anesth Analg* 2002; 95:858-65, Singbartl et al, *Anesth Analg* 2003;96:929-35. Mittermayr et al. *Anesth Analg* 2007; 105:905-17.

Dilutional coagulopathy is usually treated with fresh frozen plasma (FFP) and, if available, with cryoprecipitate. Stainsby et al. *Br J Anaesth* 2000, 85:487-91; Spahn et al. *Crit Care* 2007, 11:R17. However, critically reduced clotting factor concentrations can hardly be corrected by administering FFP because of its low concentrations of coagulation factors and its volume-expanding effects, which counterbalance the intended increase in concentration of any protein of interest. Mittermayer 2007, supra; Scalea et al. *Ann Surg,* 2008, 248:578-84; Chowdhury et al., *Br J Haematol* 2004, 125:69-73; Stanworth et al. *Br K Haematol* 2004, 126:139-52; Abdel-Wahabet al. *Transfusion* 2006, 46:1279-85. In addition, administration of FFP is associated with several complications such as onset of lung injury, multiple organ failure, and infection. Watson G A, et al, *J Trauma* 2009, 67:221-7; Sarani et al. *Crit Care Med* 2008, 36:1114-8; Dara et al. *Crit Care Med.* 2005, 33:2667-71. Moreover, the necessary thawing process delays immediate treatment, which is of special importance in the case of acute and severe bleeding.

The effect of administration of fibrinogen concentrate on dilutional coagulopathy was previously examined in vitro, in several animal models as well as in clinical practice. Fries et al. *Br J Anaesth* 2005, 95:172-7; Fries et al. *Anesth Analg* 2006, 102:347-51; Velik-Salchner et al. *J Thromb Haemost* 2007, 5:1019-25; Stinger et al. *J Trauma* 2008, 64:S79-85. Administration of fibrinogen concentrate alone normalizes clot strength, but not initiation of coagulation, as this is a thrombin-dependent reaction. Fries et al. *Br J Anaesth* 2005, 95:172-7; Fries et al. *Anesth Analg* 2006, 102:347-51; Fenger-Eriksen et al. *J Thromb Haemost* 2009, 7:795-802. Thus, combinations of fibrinogen and clotting factor complexes such as pro-thrombin complex concentrate (PCC) have been previously studied.

In particular, Fries et al. studied the effect of fibrinogen substitution on reversal of dilutional coagulopathy in an in vitro model. *British Journal of Anaesthesia,* 2006, 97(4): 460-467. Blood from 5 healthy male volunteers was diluted by 60% using lactated Ringer's solution, 4% modified gelatin solution, or 6% hydroxyethyl starch (HES) 130/0.4, as well as the combination of lactated Ringer's solution with either of 2 colloid solutions. Fries et al., *Anesth Analg;* 2006, 102:347-51. Thereafter, aliquots of diluted blood samples were incubated with 3 different concentrations of fibrinogen (0.75, 1.5, and 3.0 g/L). Measurements were performed by modified thrombelastography (ROTEM®; Pentapharm, Munich, Germany). After 60% dilution, clotting times increased, whereas clot firmness and fibrin polymerization decreased significantly. After administration of fibrinogen, clotting times decreased. Clot firmness, as well as fibrin polymerization, increased in all diluted blood samples when fibrinogen was added. The effect of in vitro fibrinogen substitution on ROTEM® variables was dependent on the fibrinogen dosage and the type of solution used to dilute the blood samples.

In another study, Fries et al. investigated the effect of fibrinogen and prothrombin complex concentrate (PCC) under conditions of haemodilution and uncontrolled haemorrhage in a porcine model. Fries et al., *British ,Journal of Anaestesia,* 2006, 97(4):460-467. After major blood loss of 65% of the estimated total blood volume, fluid volume replacement with HES (2500 ml) resulted in dilutional coagulopathy as measured by conventional coagulation tests and ROTEM® analysis. In animals receiving salvaged red blood cell concentrate only and in the placebo group, there was a small statistically significant improvement in ROTEM® parameters. However, in the treatment group, additional substitution of fibrinogen and PCC resulted in normalization of coagulation parameters. Blood loss and mortality after standardized liver injury were significantly diminished in animals treated with fibrinogen and PCC as compared with placebo.

PCC is often administered in clinical practice in the case of prolonged clotting time in critically ill patients as well as in massive bleeding situations. Schochl et al. *Anaesthesia* 2009. PCC corresponds of factors II, VII, IX and X as well as protein C and small amounts of heparin and has been used for years to treat hereditary coagulation deficiencies and for reversal of anticoagulation after administration of vitamin K antagonists. Only limited animal data are available on the use of modern PCC preparations in pigs exhibiting acquired coagulation factor deficiencies caused by massive blood loss and administration of HES. Dickneite et al. *Anesth Analg* 2008, 106:1070-7; Dickneite et al. *Br J Anaesth* 2009, 102:345-54; Dickneite et al *J Trauma* 2009.

Staudinger et al. investigated the effect of PCC on plasma coagulation in critically ill patients and pointed out that a dose of 2,000 Factor IX units of PCC (mean 30 IU/kg body weight) normalized Prothrombin Time (PT) by raising the plasma level of coagulation Factors II, VII, IX and X in patients with moderately reduced coagulation activity. Staudinger et al. *intensive Care Med* 1999, 25:1105-10. However, with regard to thrombin generation, PCC seems to be much more active than rhFVIIa. Dickneite et al *Trauma* 2009. PCC may be associated with an increased risk for thromboembolic. complication, especially in patients with acquired coagulation defects. Bagot et al. *Thromb Haemost* 2007, 98:1141-2; Warren et al. *Ann Emerg Med* 2009, 53:758-61; Kohler et al. *Thromb Haemost* 1998, 80:399-402.

Various additional methods for treatment of bleeding and blood loss have also been proposed, including supplementation of coagulation factors. See, for example, U.S. Patent Publications 2003/0129183, 2004/0198647, 2004/0237970, 2005/0282771, 2006/0025336, 2006/0211621, 2007/0232788, 2008/0014251, 2008/0188400, 2008/0267940, 2010/0093607, 2009/0098103, 2009/0148502, 2009/0175931, 2009/0232877, and 2010/0086529.

Despite the proposal and study of various compositions and methods for restoring haemostasis, there remains a need in the art for improved methods of treating haemostatic disorders such as dilutional coagulopathy.

To achieve haemostasis in patients with bleeding disorders or blood loss, a sufficient amount of thrombin and sufficient coagulable substrate (fibrinogen) are required. Key aspects in coagulation are the formation of thrombin on the platelet surface and the cleavage of fibrinogen by thrombin to form fibrin. If sufficient thrombin is formed, it converts fibrinogen to stable fibrin provided enough fibrinogen is present, which determines the firmness of the developing clot in the presence of factor XIII (FXIII).

The present invention provides for the treatment or minimization of uncontrolled bleeding using recombinant haemostatic agent(s), including recombinant human factor II FII alone or a combination of three recombinant human coagulation factors, rhII, rhFX and rhVIIa (3F), were the haemostatic agents are used with or without fibrinogen. In particular, the present invention demonstrates the efficacy of such recombinant haemostatic agents in the treatment of dilutional coagulopathy. Surprisingly, administration of rhFII alone or in combination with fibrinogen is sufficient to restore normal haemostasis. Administration of rhFII alone, or in combination with fibrinogen, can avoid the potentially serious complications of thromboembolic events that may accompany other tandard forms of ent currently provided to control bleeding disorders or blood loss.

It should be noted that reference to any publications herein should not be construed as an admission that such a publication is prior art to the inventions disclosed herein below.

SUMMARY

Treatment of a haemostatic disorder or no, finalization of haemostastis can comprise administering a clotting factor treatment selected from the group consisting of (1) FII alone; (2) PCC; and (3) a three factor combination of FII, FX, and VIIa. The clotting factor treatment (haemostatic agent(s)) can optionally be administered in combination with fibrinogen. The haemostatic agent(s) can be recombinant human factors, for example, rhFII, rhFX and rhVIIa (this three factor combination of recombinant human factors may be abbreviated 3F), or rhFII alone. In some embodiments, an effective treatment of a haemostatic disorder or normalization of haemostasis can comprise co-administering fibrinogen and rhFII. The treatment can be performed without substantial supplementation of any other clotting factor. Thus, in some embodiments, an effective treatment of a haemostatic disorder can comprise administering a clotting factor treatment selected from the group consisting of (1) FII alone, e.g., rhFII; (2) 3F; (3) fibrinogen and a combination of FII, FVIIa, and FX; (4) or fibrinogen and FII.

BRIEF DESCRIPTION OF THE DRAWINGS

FIG. 1: Blood loss per kg bodyweight in mL, after liver incision and administration of saline control, fibrinogen concentrate (fib), fibrinogen concentration in combination with PCC (PCC+fib), fibrinogen concentrate in combination with three-factor combination (ThreeF+fib) or fibrinogen concentrate in combination with recombinant human FII (FII+fib), shown as average +/−SD.

FIG. 3: Blood loss per kg bodyweight in ml after administration of (1) Saline control; (2) recombinant human FII (rhFII) at 8 mg/kg; (3) Three-factor combination corresponding to rhFII+rh FX+rhFVIIa at 4.0, 0.32 and 0.006 mg/kg, respectively (low dose); (4) Three-factor combination corresponding to rhFII+rh FX+rhFVIIa at 8.0, 0.64 and 0.012 mg/kg, respectively (high dose); (5) FEIBA VH® (activated complex concentrate (APCC); Baxter) at 40U/kg; (6) NovoSeven® (Coagulation Factor VIIa; Novo Nordisk) at a first dose of 200 μg/kg followed by a second dose of 100 μg/kg one hour later; or Haemocomplettan® HS (fibrinogen concentrate; CSL-Behring), as individual values and median (horizontal bar).

FIG. 5 (A-B): ROTEM results after administration of coagulation factors, or combinations thereof, as described for FIG. 3 above showing a) coagulation time (CT) b) maximum clot firmness (MCF) from ex-TEM (tissue factor) activated whole blood samples drawn at baseline, after dilution, after drug administration and end of experiment, respectively, shown as mean±SEM.

FIG. 6 (A-D): Thrombin generation (Calibrated Automated Thrombogram) results after administration of coagulation factors, or combinations thereof, as described for FIG. 3 above showing A) lagtime, (B) time to peak, (C) peak and (D) endogenous thrombin potential for plasma samples obtained at baseline, after dilution, after drug administration and at end of experiment, shown as mean±SEM.

FIG. 7: Concentration of thrombin-antithrombin complex in plasma samples after administration of coagulation factors, or combinations thereof, as described for FIG. 3 above drawn at baseline, after dilution, after drug administration and at end of experiment shown as median.

DETAILED DESCRIPTION

Figure 2A:
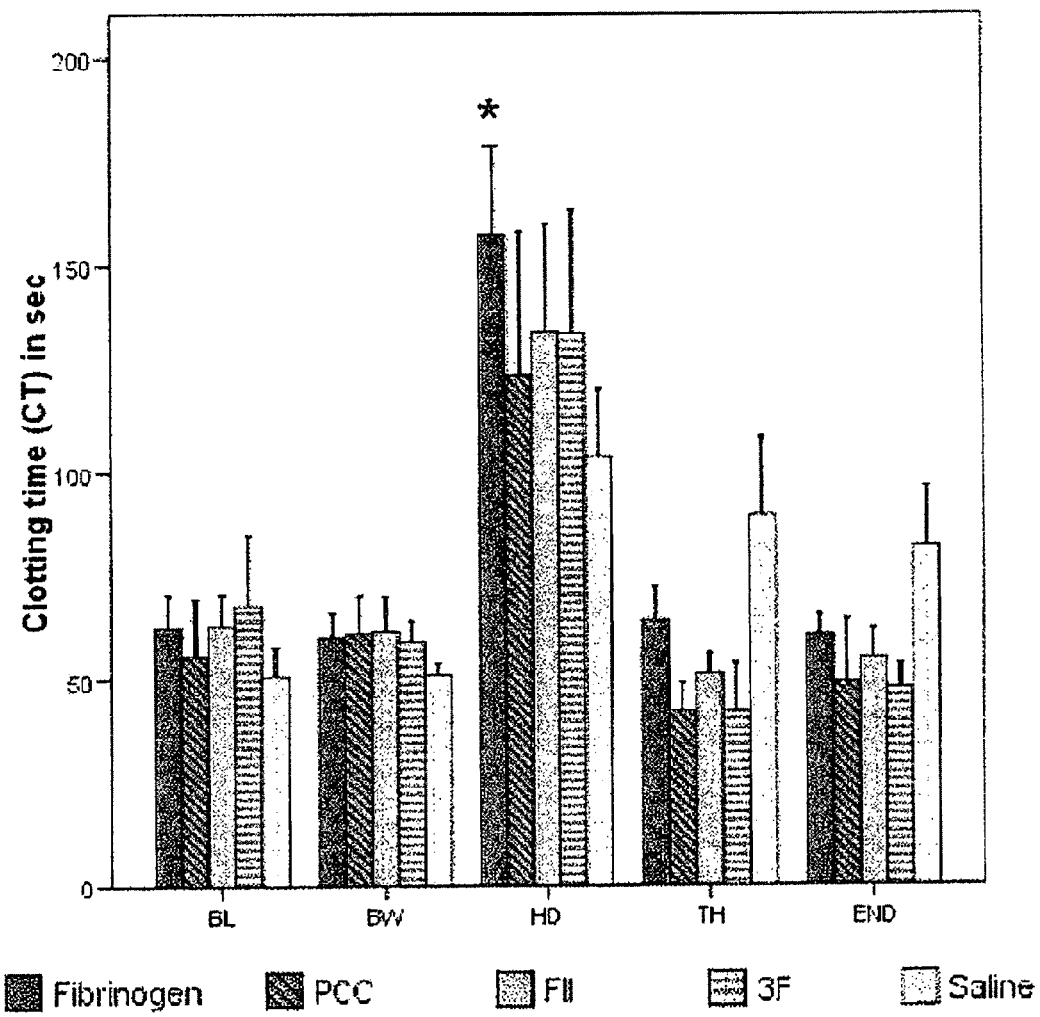
FIG. 2 (A-B): ROTEM® analysis at baseline (BL), after blood withdrawal (BW), after haemodilution (HD), after administration of the study drug (TH), and at the endpoint of observation (END). The study drugs correspond to fibrinogen concentrate (fibrinogen), fibrinogen concentration in combination with PCC (PCC), fibrinogen concentrate in combination with recombinant human FII (FII), fibrinogen concentrate in combination with three-factor combination (3F), or saline control. Clotting time (CT, in sec) (FIG. 2A) and maximum clot firmness (MCF, in mm) (FIG. 2B) are shown. Statistically significant differences (P<0.001) are shown as compared to the Saline Group and the Fibrinogen Group.

The present invention provides for the treatment of uncontrolled bleeding or normalization of haemostasis by administration of a clotting factor treatment, or a combination of one or more coagulation factors. In particular, the invention provides for the treatment of uncontrolled bleeding or normalization of haemostasis by administration of FII or a three-factor combination (FII, FX, and VIIa). In certain embodiments, the haemostatic agents or coagulation factors are recombinant human coagulation factors. In further embodiments, the coagulation factors are administered with or without fibrinogen. In certain other embodiments, the clotting factor treatment is PCC (FII, FVII, FIX and FX, optionally with small amounts of heparin).

The onset of dilutional coagulopathy and the effect of treatment can be measured by conventional coagulation tests such as rotational thrombelastometry (ROTEM®) and thrombin generation measured by Calibrated Automated Thrombogram (CAT) performed using 1 pM TF activator.

ROTEM® investigates the interaction of coagulation factors, their inhibitors, anticoagulant drugs, blood cells, specifically platelets, during clotting and subsequent fibrinolysis. The rheological conditions mimic the sluggish flow of blood in veins. Briefly, blood is placed into a disposable cuvette using an electronic pipette. A disposable pin is attached to a shaft which is connected with a thin spring and slowly oscillates back and forth. The signal of the pin suspended in the blood sample is transmitted via an optical detector system. The instrument measures and graphically displays the changes in elasticity at all stages of the developing and resolving clot. The typical test temperature is 37° C., but different temperatures can be selected. The primary result is a reaction curve which shows the elasticity over time when the clot forms or dissolves.

Four parameters describe the clotting curve in routine use. Clotting time (CT) is the latency time from adding start reagent to blood until the clot starts to form. Prolongation of CT may be a result of coagulation deficiencies, primarily coagulation factors, or heparin (depending on the test used). A shortening of CT indicates hypercoagulability.

The alpha angle is the angle of a tangent to the curve, while clot formation time (CFT) is the time from CT until a clot firmness of 20 mm point has been reached. These parameters denote the speed at which a solid clot forms and are primarily influenced by platelet function, but fibrinogen and coagulation factors also contribute. A prolonged CFT (or a lower alpha-angle) is usually caused by poor platelet function, low platelet count, fibrin polymerization disorders or fibrinogen deficiency. A shortening of CFT (or a high alpha-angle) indicate hypercoagulability. Maximum clot firmness (MCF) is the greatest vertical amplitude of the trace. It reflects the absolute strength of the fibrin and platelet clot. A low MCF is indicative of decreased platelet number or function, decreased fibrinogen level or fibrin polymerization disorders, or low activity of factor XIII. A mechanically weak clot represents a severe bleeding risk.

Variations of ROTEM® may be used to emphasize different parameters and effects. For example, EXTEM is a screening test for the (extrinsic) haemostasis system. The EXTEM reagent mildly activates haemostasis using tissue factor. The result is then influenced by extrinsic coagulation factors, platelets and fibrinogen.

Calibrated Automated Thrombogram (CAT) is described by Hemker et at (*Pathophysiol Haemost Thromb*, 2002, 32:249-253). By using a "slow" fluorogenic thrombin substrate and continuous comparison to a simultaneously run calibrator, thrombin generation can be monitored automatically. The resulting "Thrombogram" measures hypocoagulability and hypercoagulabilities in platelet poor plasma.

Treatment of a haemostatic disorder or normalization of haemostasis may comprise administering a clotting factor treatment, for example, FII and optionally FX and FVIIa or a combination of fibrinogen and FII, optionally further in combination with FX and FVIIa. The haemostatic agent(s) can be recombinant human factors, for example, rhFII, rhFX and rhVIIa, or rhFII alone. In some embodiments, an effective treatment of a haemostatic disorder can consist of administering FII or co-administering FII, FX and FVIIa, or co-administering fibrinogen with FII, and optionally further co-administering FX and FVIIa, where FII, FX and/or FVIIa can be recombinantly produced human factors.

The treatment or normalization or haemostasis can be performed without substantial supplementation of any other clotting factor. In some embodiments, a treatment of a haemostatic disorder may consist of FII or co-administration of fibrinogen and FII, where the FII can be recombinant human FII (rhFII).

The term "substantial supplementation" refers to the addition of other components, such as clotting factors in addition to those described in the present invention, in an amount whereby the effect of the one or more haemostatic agents when supplemented with such additional clotting factors is considerably different to that of the effect of administering the one or more haemostatic agents without supplementation.

As used herein, "recombinant" proteins include those proteins made by recombinant techniques. Such proteins include those which resemble the natural protein as well as those modified to enhance activity, protein half-life, protein stability, protein localization, and efficacy. See, U.S. Patent Application Publication No. US 2005/0164367, which is hereby incorporated by reference herein.

As used herein, "treatment" is a method for obtaining beneficial or desired clinical results. Beneficial or desired clinical results include, but are not limited to, alleviation of symptoms, diminishment of bleeding, stabilization of the individual, and preventing bleeding.

The phrase "consisting essentially of" is not meant to imply that other concurrent conventional patient treatments need be abstained from, rather that a treatment consisting essentially of, for example, administration of FII or co-administration of an effective amount of fibrinogen and FII is not immediately preceded by, accompanied by, or immediately followed by significant supplementation of other clotting factors, particularly protein clotting factors such as those denoted by Roman numerals V-XIII. In some embodiments, a treatment consisting essentially of administration of FII alone, or co-administration of an effective amount of fibrinogen and FII may be performed concurrently with separate procedures such as transfusion, administration of frozen platelets, recovered blood cells, fluids containing crystalloids and/or colloids, and other conventional treatments that do not comprise active supplementation of clotting factors beyond what may be endogenous in transfused blood, a frozen platelet preparation, or the like. In other embodiments, it may not be necessary or desired to concurrently perform any procedure comprising separate administration of a composition that includes significant quantities of clotting factors (for example, factors V-XIII) when performing a treatment consisting essentially of administration of an effective amount of FII, 3F, fibrinogen and FII or fibrinogen and 3F.

In some embodiments, a method of treating a traumatic bleeding disorder in a mammal in need thereof can comprise administering a clotting factor treatment selected from the group consisting of (a) PCC (FII, FX, FIX, FVII and protein C); (b) rhFII, rhFVIIa and rhFX; and (c) rhFII alone, wherein (a), (b) or (c) is provided optionally in combination fibrinogen. Likewise, a method of normalizing impaired haemostasis associated with a traumatic bleeding disorder in a mammal can comprise administering clotting factor treatment selected from the group consisting of (a) PCC (FII, FX, FIX, FVII, and protein C); (b) rhFII, rhFVIIa and rhFX; and (c) rhFII alone, wherein (a), (b) or (c) is provided optionally in combination with fibrinogen. Moreover, a method of reducing mortality resulting from a traumatic bleeding disorder an comprise administering a clotting factor treatment selected from the group consisting of (a) PCC (FII, FX, FIX, FVII, and protein C); (b) rhFII, rhFVIIa and rhFX; and (c) rhFII alone, wherein (a), (b) or (c) is provided optionally in combination with fibrinogen.

A method of treating a haemostatic disorder or normalizing haemostasis can comprise increasing maximum clot firmness (MCF), reducing clotting time (CT), and/or improving thrombin generation following hemorrhage or massive blood loss associated with a traumatic bleeding disorder in a mammal by administering a combination therapy comprising, or consisting essentially of one or more haemostatic agents including FII and optionally fibrinogen.

In any of these methods, the clotting factor treatment an be selected from the group consisting of (a) PCC (FII, FX, FIX, FVII, and protein C); (b) rhFII, rhFVIIa and rhFX; and (c) rhFII. In an embodiment, the clotting factor treatment is a combination of FII, FVIIa, and FX. In another embodiment, the clotting factor treatment is FII or rhFII alone. In other embodiments, the clotting factor treatment can be either a combination of rhFII, rhFVIIa, and rhFX or rhFII alone, substantially without supplementation of any other haemostatic factor, particularly other roman numeral denominated clotting factors. That is to say, in some embodiments, the methods can comprise administering rhFII and optionally fibrinogen substantially without supplementation of any other haemostatic factor, particularly factors V-XIII.

In alternative embodiments, the method of treating a traumatic bleeding disorder in a mammal in need thereof can consist of administering a clotting factor treatment as described above. Likewise, a method of normalizing impaired haemostasis associated with a traumatic bleeding disorder in a mammal can consist of administering a clotting factor treatment described above. Moreover, a method of reducing mortality resulting from a traumatic bleeding disorder can consist of administering a clotting factor treatment as described above.

A method of treating a haemostatic disorder or normalizing haemostasis can comprise increasing maximum clot firmness (MCF), reducing clotting time (CT), and/or improving thrombin generation following hemorrhage or massive blood loss associated with a traumatic bleeding disorder in a mammal by a method that can consist of administering a clotting factor treatment. In certain embodiments, the maximum clot firmness is increased to about 10 mm to about 40 mm, to about 10 mm to about 30 mm, to about 10 mm, to about 15 mm, to about 20 mm, to about 25 mm or to about 30 mm. In other embodiments, the clotting time is reduced by about 35 to about 75 seconds, or by about 35 seconds, by about 40 seconds, by about 45 seconds, by about 50 seconds, by about 55 seconds, by about 60 seconds, by about 65 seconds, by about 70 seconds, or by about 75 seconds. As above, the clotting factor treatment can be selected from the group consisting of (a) PCC (FII, FX, FIX, FVII, and protein C); (b) rhFII, rhFVIIa and rhFX; and (c) rhFII alone, wherein (a), (b) or (c) is provided optionally in combination with a fibrinogen. In some preferred embodiments, the clotting factor treatment is either a combination of (1) FII, FVIIa and FX; or (2) FII alone. The clotting factor treatment can comprise recombinant human factors, i.e., either a combination of (1) rhFII, rhFVIIa and rhFX; or (2) rhFII alone. In some embodiments, the methods can consist of co-administering rhFII, and optionally, co-administering fibrinogen.

"Co-administering" or "co-treatment" means administering a mixture of components, or separately administering components of a co-treatment at times that are close together, for example, administering co-administered components during temporally overlapping periods or commencing administration of one component within about an hour, or half hour, or quarter hour of the commencement or termination of administration of a co-administered component.

The components administered in the methods disclosed herein are formulated and administered using techniques that are well established in the art. For example, the fibrinogen and FII, rhFII, or 3F can be administered by intravenous injection or infusion using a pharmaceutically acceptable carrier or excipient. Carriers and excipients suitable for formulation of the active agents include any pharmaceutical agent that does not induce an immune response harmful to the individual receiving the composition, and which may be administered without undue toxicity. Pharmaceutically acceptable excipients include, but are not limited to, liquids such as water, saline, glycerol, sugars and ethanol. Pharmaceutically acceptable salts can also be included. Such salts include mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., 18th Edition, Easton, Pa., 1990).

A haemostatic disorder may be associated with any of coagulopathy (e.g., dilutional coagulopathy) traumatic bleeding, peri-surgical bleeding, post-surgical bleeding, postpartum hemorrhage, and the like. A haemostatic disorder may be associated with a blood fibrinogen concentration level of less than about 2 to about 1.5 g/L, less than about 1 g/L, or less than about 0.5 g/L. The haemostatic disorder may be associated with a blood loss of about 30% to about 85%, for example, more than about 30%, about 40%, about 45%, about 50%, about 55%, about 60%, about 70%, about 80% or about 85% of the estimated total blood volume of a mammal. In some embodiments, dilutional coagulopathy results from reestablishment of normovolemia or reestablishment of hemodynamic stabilization. Thus, a mammal in need of the treatments disclosed herein can be a mammal meeting one or more of these criteria.

Haemostatic disorders also can include hemophilia A and B, hemophilia A and B patients with inhibitory antibodies, deficiencies in coagulation factors for example, fibrinogen, FII, FV, FVII, FIX, FVIII, FX, FXI, FXII, and FXIII von Willebrand factor, combined FV/FVII deficiency, vitamin K epoxide reductase C1 deficiency, gamma-carboxylase deficiency; bleeding associated with trauma, injury, thrombosis, thrombocytopenia, stroke, coagulopathy, disseminated intravascular coagulation (DIC); over-anticoagulation associated with heparin, low molecular weight heparin, pentasaccharide, warfarin, small molecule antithrombotics (i.e. FXa inhibitors); and platelet disorders such as, Bernard Soulier syndrome, Glanzman thromblastemia, and storage pool deficiency.

A haemostatic disorder can also include bleeding related to thrombotic disorders such as deep venous thrombosis, thrombosis associated with cardiovascular disease states or malignancies, thrombosis resulting from in-dwelling catheters or other invasive surgical procedures and thrombosis associated with autoimmune diseases such as lupus.

The methods described herein may comprise or consist essentially of co-administering fibrinogen in an amount sufficient to raise the blood fibrinogen concentration above about 0.5, about 1, about 1.5 or about 2 g/L. In some embodiments, fibrinogen is administered at a dose of 12.5-200 mg/kg, for example, at a dose of e.g. about 12.5, 25, 50

100 or 200 mg/kg. In some embodiments, rhFII is administered at a dose of 1 2, 4 8, or 10 mg/kg. In some embodiments, co-administration of fibrinogen and one or more haemostatic agents results in the maintenance of approximately normalized coagulation for at least two hours after administration.

In some embodiments the active agents for a treatment can be assembled into a kit. The kit could contain fibrinogen and FII, rhFII, and/or 3F as well as any appropriate excipients, such as but not limited to saline and sucrose solution, and any additional co-factors for stabilization or effectiveness of the components of the composition, such as, but not limited to sugars, antioxidants, and albumin. In addition, the kit may comprise other elements involved in the delivery of the active agents, including a device for injection of the active agents (for example, syringe), tourniquet, and alcohol swab to clean the site of injection. Other elements may also be included in a kit including elements involved in wound closure such as suture material, needles and forceps.

While the methods disclosed herein have been described in detail with reference to embodiments thereof, it will be apparent to one skilled in the art that various changes can be made, and equivalents employed, without departing from the scope of the disclosure. Likewise, the following examples are presented as illustrative of the disclosed methods, but should not be construed as limiting the disclosed methods.

Fibrinogen or fibrinogen concentrate can be administered in addition to one or more hemostatic agents to enhance final clot strength. In certain embodiments, the combination of fibrinogen with PCC, rhFII or 3F shortens clotting time and improves thrombin generation. The administration of PCC or rhFII combined with fibrinogen can be utilized to decrease mortality in the treatment of uncontrolled hemorrhage. The administration of the combination of PCC and fibrinogen can be used to reinforce coagulation, up to 0.5 hours, one hour or two hours after administration. Thus, the use of rhFII, particularly in combination with fibrinogen, can be an alternative to PCC with comparable efficacy but with less risk for thromboembolic complications.

A treatment comprising co-administration of fibrinogen and rhFII without supplementation of any other haemostatic agents can be effective in normalizing impaired haemostasis following severe blood loss at least as high as about 60% haemodilution with less risk of complications. Co-administration of fibrinogen and the rhFII containing 3F is also effective. Moreover, an effective treatment may consist essentially of administering rhFII or 3F with or without supplementation of fibrinogen.

EXAMPLES

Example 1

Methods

Surgical Preparation and Measurements: The study was performed using fifty healthy pigs. Pre-medication of the animals was performed with azaperone (4 mg kg$^{-1}$ IM, neuroleptic agent, Stresnil™, Janssen, Vienna, Austria) and atropine (0.1 mg kg$^{-1}$ IM) one hour before commencement of the study. Anesthesia was induced and maintained with propofol (1-2 mg kg$^{-1}$ IV). For induction of analgesia, piritramide was injected (30 mg, opioid with a half-life of ~4 to 8 hours, Dipidolor™, Janssen, Vienna, Austria). For muscle relaxation 0.2 mg kg$^{-1}$ h$^{-1}$ pancuronium was injected after endotracheal anaesthesia. After intubation, a 7.5 French catheter was inserted in the femoral artery for collection of blood samples and continuous blood pressure measurement. Two 7.5 French catheters were inserted into both femoral veins for blood withdrawal, administration of colloids and crystalloids and administration of the study drug. A Swan-Ganz catheter was placed through the right $V.$ $jugularis$.

Experimental Protocol: The basal need for fluid replacement (4 ml kg$^{-1}$) was met during the entire course of the trial using crystalloids (Ringer's lactate solution). To induce a standardized dilutional coagulopathy, normovolemic hemodilution was performed with 6% HES 130/0.4 (Voluven®, Fresenius Co., Bad Homburg, Germany): blood was withdrawn from the animals via the large catheters and replaced with colloid in a ratio of 1:1. After completing hemodilution withdrawn blood was processed in a Cell Saver System (Cats®, Fresenius, Vienna, Austria), concentrated and re-transfused in order to prevent hemodynamically relevant anemia. Normovolemic hemodilution was completed when the resulting coagulopathy reached a critical level as determined by ROTEM® and usage of EXTEM reagent: clotting time (CT) >100 sec and maximum clot firmness (MCF) <40 mm. Animals were randomly assigned to either 200 mg kg$^{-1}$ fibrinogen concentrate (Haemocomplettan HS®, CSL-Behring) (Fibrinogen Group), 200 mg kg$^{-1}$ fibrinogen concentrate and 35 IU kg$^{-1}$ PCC (Beriplex®, CSL Behring, Marburg, Germany) (PCC Group), 200 mg kg$^{-1}$ fibrinogen concentrate and 4 mg kg$^{-1}$ rhFII concentrate (AstraZeneca R&D Mölndal, Sweden) (FII Group), 200 mg kg$^{-1}$ fibrinogen concentrate and a three-factor combination concentrate including 4 mg kg$^{-1}$ rhFII, 0.32 mg kg$^{-1}$ rhFX and 0.006 mg kg$^{-1}$ rhFVIIa (AstraZeneca R&D Mölndal, Sweden) (3F Group) or an equal amount of normal saline (Saline Group). The dosage of fibrinogen concentrate and PCC was based on previously published data from animal experiments. Sperry et al. $J$ $Trauma$ 2008, 64:9-14; Innerhofer P et al., $Anesth$ $Analg$ 2002, 95:858-65.

A standardized liver injury (12 cm long and 3 cm deep) was induced using a template immediately after administration of the coagulation factors or combination of coagulation factors described above. The cut was made over the right lobe of the liver. The study was blinded for the staff that performed tissue examinations, coagulation assays, documentation of the hemodynamics, liver incision, or those who participated in collecting and measuring the occurring blood loss.

After liver incision, the subsequent blood loss was assessed, as was the length of time until the animals died due to hemorrhagic shock. In addition of thrombelastometric measurements, standard coagulation assays (PT, aPTT, fibrinogen, platelet count) were performed, parameters for activated coagulation (D-dimers and TAT,) and a thrombin generation assay for estimation of the potential to form thrombin (Calibrated Automated Thrombogram, CAT) were measured.

Two hours after liver trauma the surviving animals were sacrificed with potassium infusion. Heart, lung, parts of the intestines and the kidneys were removed and evaluated for the occurrence of microvascular thrombosis.

Blood sampling and analytical methods: Arterial blood sampling was performed at baseline (BL), after blood withdrawal (BW), hemodilution (HD), therapy with study drugs (TH) and 120 min after liver incision or immediately before anticipated death (END). All blood samples were drawn from the femoral artery, whereby the first 5 ml of blood was discarded. Blood samples for ROTEM® and coagulation analysis were collected in 3 mL tubes containing 0.3 mL (0.106 mol/ L) buffered (pH 5.5) sodium citrate (Sarstedt, Nümbrecht, Germany). Blood samples for blood cell count were collected in 2.7 mL tubes containing 1.6 mg EDTA/mL (Sarstedt, Nümbrecht, Germany). Prothrombin time (PT), partial thromboplastin time (PTT-LA1), fibrinogen concentration, antithrombin (AT) and thromibin-antithrombin complex (TAT) were determined by standard laboratory methods using the appropriate tests from Dade Behring, Marburg, Germany, and the Amelung Coagulometer, Baxter, UK. For D-dimer measurements the assay D-dimer 0020008500® (Instrumentation Laboratory Company, Lexington, USA) was used. Blood cell count was performed using the Sysmex Poch-100i® counter (Sysmex, Lake Zurich, Ill., USA). Thromboelastometry (ROTEM®, Pentapharm, Munich, Germany) was used for functional assessment of the coagulation system. For acceleration and better standardization, the EXTEM reagent was used. Luddington, *Clin Lab Haematol* 2005, 27:81-90.

The Calibrated Automated Thrombogram (CAT) assay was performed in round-bottom 96-well plates (Greiner microlon, U-shaped, high binding, USA). Citrated plasma samples (80 µl) and trigger solution (20 µl) (PPP reagent low Cat# TS31.00, Thrombinoscope, Maastricht. The Netherlands) containing 1 pM TF were mixed in sample wells. Parallel thereto, a calibrator (Cat # TS20.00, Thrombinoscope) was analyzed by mixing 20 µl calibrator and 80 µl pooled citrated normal pig plasma in wells coupled to the sample wells. Then the plate was moved to a fluorometer (Ascent reader, Thermolabsystems OY, Helsinki, Finland) and 20 µl of FluCa solution (Cat # TS50.00, Thrombinoscope) containing fluorogenic substrate and $CaCl_2$ was dispensed by the instrument. The fluorogenic signal was measured at $\lambda$ex 390 nm, $\lambda$em 460 nm during 60 min. The 96-well plate was kept on a 37° C. heating block during addition of the reagents. Commencement of thrombin activity (lagtime), time to peak thrombin activity (ttPeak), peak thrombin activity (Peak), and total thrormibin activity, i.e. endogenous thrombin potential (ETP) were calculated using the software Thrombinoscope (version 3.0.0.29) from Thrombinoscope BV (Maastricht, Netherlands).

Statistical Analysis: All statistical analyses were performed using the SPSS 15.0 statistical package (SPSS, Chicago, Ill.). Shapiro-Wilk's Test was used to test for normality. Those variables not normally distributed were logarithmically transformed to enable parametric analysis. Applying a hierarchical procedure, an analysis of variance was performed (ANOVA) to detect overall group and time effects ($P<0.05$ was considered significant). In the case of significant differences, an analysis of variance was performed (ANOVA) to detect differences between groups. The Bonferroni-Holm procedure was used for correction of multiple comparisons. $P<0.005$ was considered significant. In the case of significant differences paired T tests within and independent T tests between groups were performed, $P<0.001$ was considered significant. Survival between groups was analyzed using Kaplan-Meier methods with log rank (Mantel Cox) comparison of cumulative survival by treatment group.

Results 50 pigs with a mean weight of 36.98 kg (±4.23) and an age between four and five months were examined. At baseline, no statistically significant differences were detected between groups with regard to hemodynamic or coagulation parameters, platelet or red blood cell count. All coagulation test results were within the normal range. Velik-Salchner et al. *Thromb Res* 2006, 117:597-602.

Survival time: Animals treated with fibrinogen combined with rhFII ($P=0.029$) or with PCC ($P=0.017$) lived significantly longer following liver injury with uncontrolled hemorrhage than did those in the control group. All groups of animals treated with at least one blood factor had increased survival times as compared to the control group, while fibrinogen alone and the combination of fibrinogen with 3F showed a similar effect on survival following liver injury compared to the control group. One animal died due to a thromboembolic complication immediately following administration of PCC.

Blood Loss: As shown in FIG. 1, following liver injury with uncontrolled hemorrhage, blood loss was significantly decreased in all groups as compared to the saline group.

ROTEM®: Clotting time (CT) was significantly decreased after administration of fibrinogen combined with PCC or with 3F as compared to treatment with saline or fibrinogen alone. As shown in FIG. 2a, at the end of the observation period (END), CT was still significantly shortened in the animals treated with the combination of fibrinogen and 3F as compared to saline or fibrinogen alone. The combination of fibrinogen and PCC significantly shortened CT as compared to saline.

As shown in FIG. 2b, maximum clot firmness (MCF) significantly increased upon administration of fibrinogen combined with 3F or rhFII as compared to treatment with saline alone. After dilution, MCF significantly decreased by the same amount in all groups. Following the administration of fibrinogen, MCF significantly increased as compared to the control animals treated with saline. At the end of the observation period, MCF was still significantly increased in the pigs that received the combination of fibrinogen and 3F concentrate (3F Group) or fibrinogen and rhFII as compared to the saline group.

Thrombin Generation (CAT): Lagtime and time to peak did not differ within the groups. Administration of fibrinogen combined with PCC, rhFII or with 3F resulted in a significantly higher peak value than in animals treated with fibrinogen alone. Compared with the control group, peak value was also significantly increased following administration of fibrinogen and rhFII as well as fibrinogen and 3F. Two hours after liver injury, the peak value was significantly increased in animals treated with the combination of fibrinogen and PCC as compared to all other groups. Animals treated with the combination of fibrinogen and rhFII as well as fibrinogen and 3F had a significantly higher ETP than did animals treated only with fibrinogen (#), while the combination of fibrinogen and rhFII also resulted in significantly higher ETP as compared to the control group. At the end of the observation period, the combination of fibrinogen and PCC had a significantly higher ETP than all other groups.

CONCLUSION

As demonstrated above, administration of PCC or rhFII in combination with fibrinogen, as compared to saline or fibrinogen alone, resulted in a significant decrease in blood loss following normovolemic hemodilution and liver injury. The administration of PCC or rhFII in combination with fibrinogen also resulted in animals living significantly longer following liver injury. Clotting time was significantly shortened with administration of rFII in combination with fibrinogen as compared to controls, and the maximum clot firmness also significantly increased with treatment of rhFII in combination with fibrinogen. These results demonstrate that administration of rhFII (in this case, in combination with fibrinogen) is an efficacious treatment sufficient to restore normalized haemostasis, prevent blood loss and decrease mortality. The use of rhFII in the treatment of bleeding disorders and blood loss is thus effective and could avoid the potentially serious complications of thromboembolic events that may accompany the administration of a combination of multiple coagulation factors.

Example 2

Methods

Anaesthesia and Maintenance of Homeostasis: The pigs were premedicated with intra muscular Dormicum (2 mg/kg) and Ketaminol (10 mg/kg). After approximately 20 min a polyethylene catheter (Venflon 1.0×32 mm, Becton Dickinson, Helsingborg, Sweden) was inserted into an ear vein to be used for administration of anaesthetics and Ringer solution. The pigs were initially anaesthetized with pentobarbital sodium (Apoteksbolaget, Umeå, Sweden), given intra venously as a bolus dose (15 mg/kg) to make intubation possible. During the experiment the anaesthesia was maintained with a subsequent infusion of pentobarbital (10-15 mg/kg/h) complemented by 1.8% isoflurane (Isoba® vet, Schering-Plough, Denmark) during the preparation. The pigs were ventilated (Servo Ventilator 9000, Siemens Elema, Solna, Sweden) with room air supplied with 10% $O_2$. The respiratory rate was held constant at 15 cycles and end tidal $CO_2$ was kept at ~5.5 kPa by regulating the tidal volume. Ringer solution (Fresenius Kabi A S, Halden, Norway) 1.5 mL/kg/h was given continuously to replace fluid loss. Body temperature was maintained at 36 to 39° C. throughout the experiment by covering the animals and by external heating. At the end of the experiment the animals had a lethal dose of pentobarbital (>150 mg/kg).

Surgical Preparations: A polyethylene catheter (Intramedic PE-200 Clay Adams, Parsippany, N.J., USA) was inserted in the right femoral artery for continuous arterial pressure measurement and for collection of blood samples. Polyethylene catheters (Intramedic PE-200 Clay Adams, Parsippany, N.J., USA) were advanced into both fe oral veins for blood withdrawal and administration of processed red cells (PRC), hydroxyethyl starch (HES) and study drug/vehicle. A fourth polyethylene catheter (Intramedic PE-200 Clay Adams, Parsippany, N.J., USA) for monitoring central venous pressure (CVP) was placed in the right jugular vein. Body temperature was measured by a rectal probe. Finally a midline laparotomy, approximately 35 cm, was performed to uncover the liver. Until the liver incision was made, the wound was closed with haemostatic forceps and protected from drying by saline soaked swabs.

Experimental Protocol: After baseline blood samples (BS0) the animals underwent an isovolaemic and normothermic exchange of ~60% of their total blood volume (70 mL/kg) with HES 60 mg/mL (Voluven®, Fresenius Kabi AB, Uppsala, Sweden). As much blood as possible was withdrawn with 50 mL syringes prepared with 5 mL 0.109 M sodium citrate, until mean arterial blood pressure (MAP) reached a critical level of 30 mmHg to 35 mmHg. The animals were then left resting until MAP increased to a stable level (approximately 10 min).

Blood withdrawing was then continued until MAP dropped down to minimum 30 mmHg and HES was immediately administered i.v. (1 mL HES:1 mL blood) by means of a pressure cuff. Normally it is difficult to take the calculated volume of blood needed to establish coagulopathy during the first blood-HES exchange round. If the level of coagulopathy, checked with ROTEM analysis, is too low more blood is withdrawn and replaced with HES (1:1 although blood is diluted after the first exchange round). During the second and all following rounds, mean arterial pressure will not drop below 60 mmHg and there is no need for any recovery break. To maximize the volume of blood withdrawn in the first exchange round even though MAP is dropping, phenylephrine hydrochloride (Apoteket AB, Mölndal, Sweden) can be administered i.v. to squeeze blood out from peripheral vessels. Phenylephrine hydrochloride (ca 2 mL of 0.1 mg/ml) is given after the 10 min recovery break when MAP has dropped to approximately 40 mmHg During the short and immediate increase in MAP some additional syringes can be filled with blood.

The shed blood was processed using the quality wash program on a cell saver device (CATS,® Fresenius Kabi AB, Uppsala, Sweden) and after volume resuscitation with HES the animals received an appropriate volume of processed red cells in order to keep the haemoglobin value above 50 g/L and thereby avoid early death from severe anaemia. ROTEM analysis was performed after the haemodilution to determine the extent of coagulopathy. Criterias for coagulopathy were as follows: $CT_{Ex-TEM} \geq 100$ s and MCF ≤40 mm. After established coagulopathy a blood sample was collected (BS2). Then the study drug was administered. The study drugs corresponded to the following: (1) Saline control; (2) recombinant human FII (rhFII) at 8 mg/kg; (3) Three-factor combination corresponding to rhFII+rh FX+rhFVIIa at 4.0, 0.32 and 0.006 mg/kg, respectively (low dose); (4) Three-factor combination corresponding to rhFII+rh FX+rhFVIIa at 8.0, 0.64 and 0.012 mg/kg, respectively (high dose); (5) FEIBA VH® (anti-exhibitor coagulant complex (AICC); Baxter) at 40 U/kg; (6) NovoSeven® (Coagulation Factor VIIa; Novo Nordisk) at 200+100 µg/kg; or Haemocomplettan® HS (fibrinogen concentrate; CSL-Behring). Ten (10) minutes after completed infusion another blood sample was collected (BS3). A standardized incision was made by placing a homemade template on the right liver lobe and pulling a surgical blade (no. 11) through a slit in the template (length 8 cm, depth 3 cm) to induce uncontrolled bleeding. Maximum observation time after liver incision was 120 min. Just before death a last blood sample was collected (BS4). Blood was suctioned out of the abdomen and total blood loss as well as survival time was determined. Death was defined as pulse-less electrical activity, MAP below 15 mmHg or end tidal carbon dioxide below 1.5 kPa.

Blood Sampling: Arterial blood was collected in citrated tubes (S-Monovette® 9 NC/2.9 mL, Sarstedt, Nümbrecht, Germany) for ROTEM measurements and plasma was saved for thrombin generation and Thrombin-Antithrombin complex analyses. Blood for determining plasma concentration of recombinant human Factor II (rhFII), recombinant human Factor X (rhFX), FVIIa, human fibrinogen and cell counting was collected in potassium EDTA tubes (S-Monovette® 2.6 mL, K3E, Sarstedt, Nümbrecht, Germany).

Whole Blood Analyses

ROTEM: Throughout the experiment serial blood samples were obtained to assess the competence of the haemostatic system regarding development of clot elasticity using standard coagulation tests (EXTEM,® INTEM,® Pentapharm GmbH, Munich, Germany) in rotational thromboelastometry (ROTEM® , Pentapharm GmbH, Munich, Germany). Commercial available reagents were used except for calcium cloride solution that was prepared in-house with similar concentration as the commercial available solution. Procedure instructions from the manufacturer were followed. In this study, coagulation time (CT), clot formation time (CFT) and maximal clot firmness (MCF) were evaluated.

Blood Gases and Electrolytes: Arterial blood gases, acid-base parameters and electrolytes were analysed during the experiment (ABL 700, Radiometer Medical ApS, Brönshöj, Denmark). Analyses were performed according to manufacturer's instructions. All animals presented a good blood gas status throughout the experiments.

Cell Counting: To monitor possible variations in blood cell concentrations, arterial blood samples were analysed in an automated cell counter instrument (KX-21N, Sysmex, Kobe, Japan) at all blood sampling occasions. Analyses were performed according to manufacturer's instructions.

Plasma Analyses

Thrombin-Antithrombin Complex (TAT): Plasma levels of TAT were measured using a sandwich enzyme immunoassay (Enzygnost® TAT micro, Dade Behring GmbH, Marburg, Germany). Instructions from the manufacturer were followed. If concentrations >90 µg/mL were obtained, the samples were diluted 10 times in diluent buffer and reanalysed. If clots were observed in plasma samples, they were not analysed for TAT.

CAT: The CAT assay was performed as described in Example 1.

Results

Data analysis: Mean arterial pressure, central venous pressure, and heart rate data were collected using in-house software (PharmLab V6.0, AstraZeneca R&D Mölndal). Results are presented as descriptive statistics with mean values±standard error of the mean (SEM) except for whole blood coagulation time and TAT concentration results. These results are presented as median values because outliers in these data affected the mean value in a misleading way. The last blood sample in each experiment, called "end of experiment," is taken prior to death which occurs at different experimental time points for most animals.

Blood Loss: FIG. 3 shows blood loss per kg bodyweight in ml after administration of vehicle, test and control substances and liver incision. Data is shown as individual values with the median represented by a horizontal bar.

Figure 4:
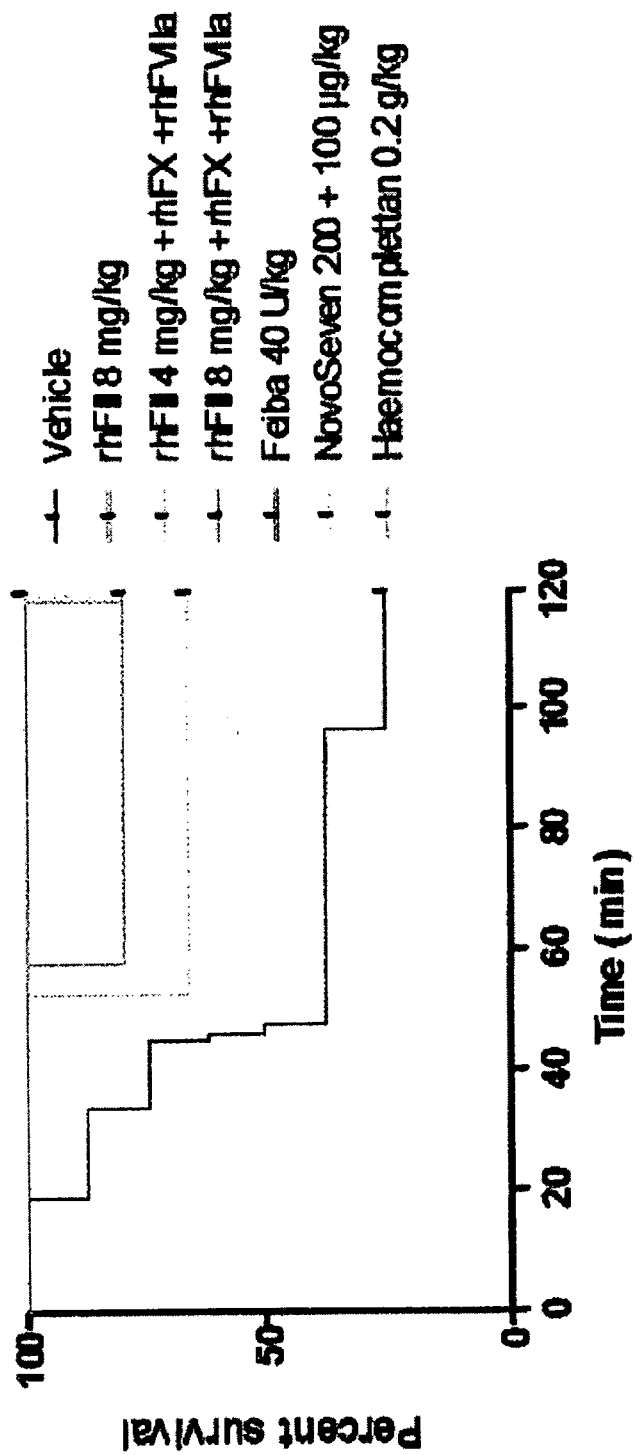
FIG. 4: Shows the survival curves for the different treatment groups. In the vehicle group 25% of the animals survived throughout the whole experiment. The survival for 2 h of observation time in the treatment groups were for the lower dose of the Three-factor combination 67%, the higher dose Three-factor combination, NovoSeven® and Haemocomplettan® 80%, rhFll and FEIBA® 100%, respectively.

Survival time: FIG. 4 shows the survival curves for the different eatment groups. In the vehicle group 25% of the animals survived throughout the whole experiment. The survival for 2 h of observation time in the treatment groups were for the lower dose of the Three-factor combination 67%, the higher dose Three-factor combination, NovoSeven® and Haemocomplettan® 80%, rhFII and FEIBA® 100%, respectively ROTEM: The results from EXTEM activation, i.e. activation via TF, of whole blood samples drawn at baseline, after dilution, after drug administration and at the end of experiment are shown in FIGS. 5A and 5B. At baseline, CT and MCF are similar for all treatment groups. After dilution, CT increases two times the baseline level while MCF decreases to about half the level at baseline. After dilution, both variables show larger variability between the groups compared to baseline. After administration of treatments, CT for all included treatments was similarly shifted towards baseline values without complete normalisation. The effect on MCF by the different treatments was small except for Haemocomplettan® (fibrinogen) that showed an almost normalised MCF after drug administration.

CAT: Results from calibrated automated thrombogram analysis of plasma samples drawn at baseline, after dilution, after drug administration and at the end of experiment are shown in FIGS. 6(a-d).

After dilution, lagtime (LT) and time to Peak (ttPeak) decreased while Peak and endogenous thrombin potential (ETP) increased compared to baseline values. After the substances had been administered LT increased about 50% for rhFII and a slight increase was noted for Haemocomplettan® while the other substances resulted in slight decreases of LT. Further on, ttPeak showed the same pattern as LT. The Peak values were increased for rhFII by 100%, Three-factor combination (low dose) by 30%, Three-factor combination (high dose) by 150% and FEIBA® by 150% compared to the value after dilution. Vehicle, NovoSeven® and Haemocomplettan® did not change Peak compared to the value immediately after dilution. Finally the ETP values were increased by almost 200% for rhFII, Three-factor combination (high dose) and FEIBA® compared to the values after the dilution step. The ETP for the low dose Three-factor combination was increased by approximately 30% compared to after dilution.

At the end of the experiment, LT corresponded to the same period of time as was the case after dose administration, with the exception that rhFII had decreased to the same level as after the dilution step. The ttPeak values were as for LT. The situation for Peak showed that all substance groups except FEIBA® had returned to the level found after finalised dilution. FEIBA® still showed Peak comparable to the level found immediately after administration of substance. ETP values at the end of the experiment were all similar to the Peak pattern.

TAT: As shown in FIG. 7, the levels of TAT were similar in all treatment groups after the dilution step. When drugs had been administered, an increase in TAT levels between 2-3 times was seen for all treatments containing prothrombin, i.e. the three-factor combinations, rhFII and FEIBA®. At the end of the experiment, the pattern obtained after drug administration was still consistent, with even more increase in TAT levels for the prothrombin-containing treatments except for rhFII alone, which shoved a decreased TAT level as compared to after administration. Haemocomplettan® and NovoSeven® also had increased TAT levels at the end of experiment compared to both after dilution and after administration by a factor of 2 to 3.

CONCLUSION

As demonstrated above, administration rhFII alone, as compared to saline or other treatments, resulted in a significant decrease in blood loss following normovolemic hemodilution and liver injury, Throbogram analyses revealed an increased in lagtime of about 50% for rhFII alone, and increase in Peak value for rhFII alone by 100% and an increase in ETP value for rhFII alone by almost 200%. These results further demonstrate that administration of rhFII alone is an efficacious treatment sufficient to restore normalized haemostasis, prevent blood loss and increase survival time.

The use of rhFII alone ortherwise of the three-factor combination have not previously been tested in a complex animal model of uncontrolled bleeding due to dilutional coagulopathy. Thus, the present invention, provides for the first tinge, the efficacy of rhFII alone, or the efficacy of 3F for the treatment of bleeding disorders and blood loss. As described in Example 2 above, the TAT levels and thrombin generation data at the end of the experiment decreased to the pre-administration levels for all samples. For the administration of coagulation factors, such as rhFII alone, this may be advantageous as it enables a better modulation of a trtreatmentregimen during the course a critical bleeding episode or period of blood loss. A longer duration time may not allow for necessary adjustments in treatment regimens. Furthermore, the administration of rhFII alone, as discussed above, can avoid, during treatment, the potentially serious complications of trombocembolic events that sometimes accompany the administration of a combination of multiple coagulation factors.

What is claimed is:

1. A method of normalizing impaired haemostasis associated with dilutional coagulopathy in a mammal in need thereof comprising administering a clotting factor treatment selected from the group consisting of: (1) recombinant human FII (rhFII), (2) a combination of rhFII and recombinant human FVIIa (rhVIIa), (3) a combination of rhFII, rhVIIa, and recombinant human FX (rhFX), (4) fibrinogen and a combination of rhFII, rhFVIIa, and rhFX, (5) fibrinogen and rhFII, and (6) fibrinogen and a combination of rhFII and rhVIIa, wherein administration of said clotting factor treatment is performed without co-administration of any other coagulation factors selected from human coagulation factors FV-FXIII.

2. The method of claim 1, wherein said impaired haemostasis associated with dilutional coagulopathy is associated with massive blood loss or a traumatic bleeding event.

3. The method of claim 2, wherein said hemorrhage or traumatic bleeding event is associated with peri-surgical bleeding, post-surgical bleeding or postpartum hemorrhage.

4. The method of claim 1, wherein the mammal in need of treatment has a blood fibrinogen concentration level of less than 2 g/L, less than 1 g/L, less than 0.5 g/L, less than 200 mg/dL, less than 150 mg/dL, less than 100 mg/dL, or less than 50 mg/dL g/L.

5. The method of claim 1, wherein said dilutional coagulopathy is associated with a blood loss of greater than 30%, greater than 40%, greater than 50%, greater than 60%, greater than 70%, greater than 80% or greater than 85% of the estimated total blood volume of a mammal.

6. The method of claim 1, wherein said dilutional coagulopathy results from reestablishment of normovolemia or haemodynamic stabilization.

7. The method of claim 1, wherein fibrinogen is administered in an amount sufficient to raise the blood fibrinogen concentration above 0.5 g/L, above 1 g/L, above 1.5 g/L, or above 2 mg/L.

8. The method of claim 1, wherein fibrinogen is administered at a dose of 12.5 to 200 mg/kg.

9. The method of claim 1, wherein the clotting factor is rhFII and is administered at a dose of 1 to 10 mg/kg.

10. The method of claim 1, wherein the clotting factor treatment is administered at a dose that reduces clotting time by 40 seconds to 60 seconds.

11. The method of claim 1, wherein the clotting factor treatment is administered at a dose that increases maximum clot firmness to 10 mm to 30 mm.

12. The method of claim 1, wherein administration of said clotting factor treatment results in the maintenance of normalized coagulation for at least two hours after administration.

13. A method of normalizing impaired haemostasis associated with dilutional coagulopathy in a mammal in need thereof, the method comprising administering a clotting factor treatment selected from the group consisting of: (1) recombinant human FII (rhFII), and (2) fibrinogen and rhFII; wherein fibrinogen is administered at a dose of 12.5 to 200 mg/kg, rhFII is administered at a dose of 1 to 10 mg/kg and administration of said clotting factor treatment is performed without co-administration of any other coagulation factors from among the human coagulation factors FV-FXIII.

14. The method of claim 13, wherein fibrinogen is administered in an amount sufficient to raise the blood fibrinogen concentration above 0.5 g/L, above 1 g/L, above 1.5 g/L, or above 2 mg/L.

15. The method of claim 13, wherein the mammal in need of treatment has a blood fibrinogen concentration level of less than 2 g/L, less than 1 g/L, less than 0.5 g/L, less than 200 mg/dL, less than 150 mg/dL, less than 100 mg/dL, or less than 50 mg/dL g/L.

16. The method of claim 13, wherein said dilutional coagulopathy is associated with a blood loss of greater than 30%, greater than 40%, greater than 50%, greater than 60%, greater than 70%, greater than 80% or greater than 85% of the estimated total blood volume of a mammal.

* * * * *